United States Patent [19]

Ochoa et al.

[11] Patent Number: 5,556,763
[45] Date of Patent: Sep. 17, 1996

[54] EVALUATION AND TREATMENT OF PATIENTS WITH PROGRESSIVE IMMUNOSUPPRESSION

[75] Inventors: Augusto C. Ochoa, Frederick; Dan L. Longo, Kensington; Paritosh Ghosh, Frederick; Howard A. Young, Gaithersburg, all of Md.

[73] Assignee: The United States of America as represented by the Department of Health and Human Services, Washington, D.C.

[21] Appl. No.: 34,832

[22] Filed: Mar. 17, 1993

Related U.S. Application Data

[63] Continuation-in-part of Ser. No. 31,434, Mar. 15, 1993, abandoned, which is a continuation-in-part of Ser. No. 987,966, Dec. 11, 1992, which is a continuation-in-part of Ser. No. 863,262, Apr. 6, 1992, Pat. No. 5,296,353.

[51] Int. Cl.$^6$ .................. A61K 49/00; G01N 33/574
[52] U.S. Cl. .................. 435/7.23; 424/9.2; 424/93.71; 435/6; 435/7.24; 436/501
[58] Field of Search .................. 435/6, 7.23, 7.24, 435/975; 436/501; 530/350, 387.1; 424/9, 9.2, 93.71

[56] References Cited

U.S. PATENT DOCUMENTS

| | | | |
|---|---|---|---|
| 4,690,915 | 9/1987 | Rosenberg | 514/2 |
| 5,024,940 | 6/1991 | Brenner et al. | 435/69.1 |
| 5,061,488 | 10/1991 | Wiltrout et al. | 424/85.2 |
| 5,096,707 | 3/1992 | Wiltrout et al. | 424/195 |
| 5,124,251 | 6/1992 | Lanier et al. | 435/7.21 |
| 5,250,431 | 10/1993 | Rudd et al. | 425/240.2 |
| 5,272,082 | 12/1993 | Santoli | 435/240.2 |
| 5,296,353 | 2/1994 | Ochoa | 435/534 |
| 5,316,763 | 5/1994 | Ochoa et al. | 424/85.2 |

FOREIGN PATENT DOCUMENTS

WO88/09183  1/1988  WIPO.

OTHER PUBLICATIONS

Irving et al., "The Cytoplasmic Domain of the T Cell Receptor ζ Chain is Sufficient to Couple to Receptor–Associated Signal Transduction Pathways" (Mar. 1991) *Cell* 64: 891–901.

Letourneur et al., "Activation of T Cells by a Tyrosine Kinase Activation Domain in the Cytoplasmic Tail of CD3 ε" (Jan. 1992) *Science* 255: 79–82.

Klausner et al., "T Cell Antigen Receptor Activation Pathways: The Tyrosine Kinase Connection" (Mar. 1991) *Cell* 64: 875–878.

Smyth et al., "Regulation of Lymphokine–Activation Killer Activated Killer Activity and Pore–Forming Protein Gene Expression in Human Peripheral Blood CD8$^+$ T Lymphocytes" *Immunol.* 146: 3289–3297.

Schmitt–Verhulst et al., "Pleiotropic loss of activation pathways in a T-Cell receptor α–chain delection variant of a cytolytic T-Cell clone" *Nature* 325: 628–631.

Klausner et al., "The T Cell Antigen Receptor: Insights into Organelle Biology" *Annu. Rev. Cell Biol.* 6: 403–431.

Buferne et al., "Role of CD3 δ in Surface Expression of the TCR/CD3 Complex and in Activation for Killing Analyzed with a CD3 δ–Negative Cytotixic T Lymphocyte Variant" *J. Immunol.* 148: 657–664.

Blumberg, et al., "Structure of the T-cell antigen receptor: Evidence for two CD3 ε subunits in the T–cell receptor–CD3 complex" (Sep. 1990) *Proc. Natl. Acad. Sci. USA* 87:7720–7724.

Patel et al., "Multiple Kinases and Signal Transduction" (Apr. 1987) *J. Biol. Chem.* 262:5831–5838.

Samelson et al., "Antigen Activation of Murine T Cells Induces Tyrosine Phosphorylation of a Polypeptide Associated with the T Cell Antigen Receptor" (Sep. 1986) *Cell* 46:1083–1090.

Hsi et al., "T Cell Activation Induces Rapid Tyrosine Phosphorylation of a Limited Number of Cellular Substrates" (Jun. 1989) *J. Biol. Chem.* 264: 10836–10842.

June et al., "Increases in Tyrosine Phosphorylation are Detectable before Phospholipase C Activation After T Cell Receptor Stimulation" (Mar. 1990) *J. Immunol.* 144: 1591–1599.

Loeffler et al., "Immunosuppression in Tumor Bearing Mice: Functional and Molecular Basis" (Mar. 1991) First International Symposium on Combination Therapies, George Washington School of Medicine, Abstract No. 6.

Samelson et al., "Association of the fyn protein–tyrosine kinase with the T–cell antigen receptor" (Jun. 1990) *Proc. Natl. Acad. Sci. USA* 87:4358–4362.

Weiss et al., "Role of T3 surface molecules in human T–cell activation: T3–dependent activation results in an increase in cytoplasmic free calcium" (Jul. 1984) *Proc. Natl. Acad. Sci. USA* 81: 4169–4173.

Imboden et al., "Transmembrane Signalling by the T Cell Antigen Receptor" (Mar. 1985) *J. Exp. Med.* 161: 446–456.

Ullman et al., "Transmission of Signals from the T Lymphocyte Antigen Receptor to the Genes Responsible for Cell Proliferation and Immune Function: The Missing Link" (1990) *Ann. Rev. Immul.* 8: 421–452.

(List continued on next page.)

*Primary Examiner*—David Saunders
*Attorney, Agent, or Firm*—Foley & Lardner

[57] ABSTRACT

A soluble immunosuppressive factor present in serum derived from tumor-bearing mammals, is associated with changes in TCR protein subunit levels, T lymphocyte signal transduction pathway proteins. These changes provide a method of determining the level of immunosuppression in a mammal by determining the level of expression of at least one selected TCR subunit protein, a protein in the T lymphocyte signal transduction pathway, or of the NF-κB/rel family and comparing the level and pattern to that found in non-immunosuppressed individuals. The method is useful to identify patients having T lymphocytes capable of activation for immunotherapy and for identifying agents which cause or reverse immunosuppression. An isolated immunosuppressive factor associated with the level of expression of the proteins is useful for suppressing the immune response, for example, in organ transplantation.

11 Claims, 5 Drawing Sheets

OTHER PUBLICATIONS

Weiss et al., "The Role of the T3/Antigen Receptor Complex in T–Cell Activation" (1986) *Ann. Rev. Immunol.* 4: 593–619.

Frank et al., "Structural Mutations of the T Cell Receptor ζ Chain and its Role in T Cell Activation" *Science*, 249:174–177.

Rodewald et al., "The High Affinity FCε Receptor γ Subunit (FCεRIγ) Facilitates T Cell Receptor Expression and Antigen/Major Histocompatibility Complex–driven Signaling in the Absence of CD3ζ and CD3η" (Aug. 1991) *J. Biol. Chem.* 266: 15974–15978.

Hommel–Berrey et al., "Receptor Modulation and Early Signal Transduction Events in Cytotoxic T Lymphocytes Inactivated by Sensitive Target Cells" (Nov. 1991) *J. Immunol.* 147:3237–3243.

Sussman et al., "Failure to Synthesize the T Cell CD3–ζ Chain: Structure and Function of a Partial T Cell Receptor Complex" (Jan. 1988) *Cell* 52: 85–95.

Chan et al., "The ζ chain is associated with a tyrosine kinase and upon T–cell antigen receptor stimulation associates with ZAP–70, a 70–kDa tyrosine phosphoprotein" (Oct. 1991) *Proc. Natl. Acad. Sci. USA* 88:9166–9170.

Weissman et al., "Role of the zeta chain in the expression of the T cell antigen receptor: genetic reconstitution studies" (1989) *EMBO J.* 8: 3651–3656.

Weissman et al., "Tyrosine Phosphorylation of the Human T Cell Antigen Receptor ζ–chain: Activation via CD3 but not CD2" (Nov. 1988) *J. Immunol.* 141: 3532–3536.

Baniyash et al., "The T Cell Antigen Receptor ζ Chain is Tyrosine Phosphorylated upon Activation" (Dec. 1988) *J. Biol. Chem.* 263: 18225–18230.

Wegener et al., "The T Cel Receptor/CD3 Complex is Composed of at Least Two Autonomous Transduction Modules" (Jan. 1992) *Cell* 68:83–95.

Furue et al., "Coordinate Expression of src Family Protooncogenes in T Cell Activation and Its Modulation by Cyclosporine," (1990) *J. Immunol.* 144: 736–739.

C. M. Loeffler et al., *Cancer Research* 51: 2127–2132 (1991).

*B. M. Biochemica*, Nov. 1989 PAI–9.

Anderson et al. "Augmentation of Cell Number and LAK Activity in Peripheral Blod Mononuclear Cells Activated With Anti–CD3 And Interleukin–2", *Cancer Immunol. Immunother.* 27: 82–88 (1988).

Anderson et al. "Anti–CD3 + IL–2 Stimulated Murine Killer Cells in Vitro Generation and In Vivo Antitumor Activity", *J. Immunol. 142(4): 1383–1394 (1989)*.

Ochoa et al. "Lymphokine–Activated Killer Activity in Long–Term Cultures With ANti–CD3 Plus Interleukin2: Identification and Isolation of Effector Subsets", *Cancer Research* 49:963–968 (1989).

Kang, et al., "NF–κB Subunit Regulation in Nontransformed CD4$^+$ *T Lymphocytes*" (Jun. 1992) *Science* vol. 256: 1365–1488.

P. Gosh et al, Cancer Research, 54, 2969–2972, 1994.

P. Gosh et al, Proc. Natl. Acad. Sci., USA, 90, 1696–1700, 1993.

A. Granelli–Piperno et al, Jour. Exper. Med., 172, 1869–1872, 1990.

P. Gosh et al, Jour. Cell, Biochem., Suppl. O (18D), 400, 1994.

P. A. W. Edwards, Biochemical Journal, 200, 1–10, 1981.

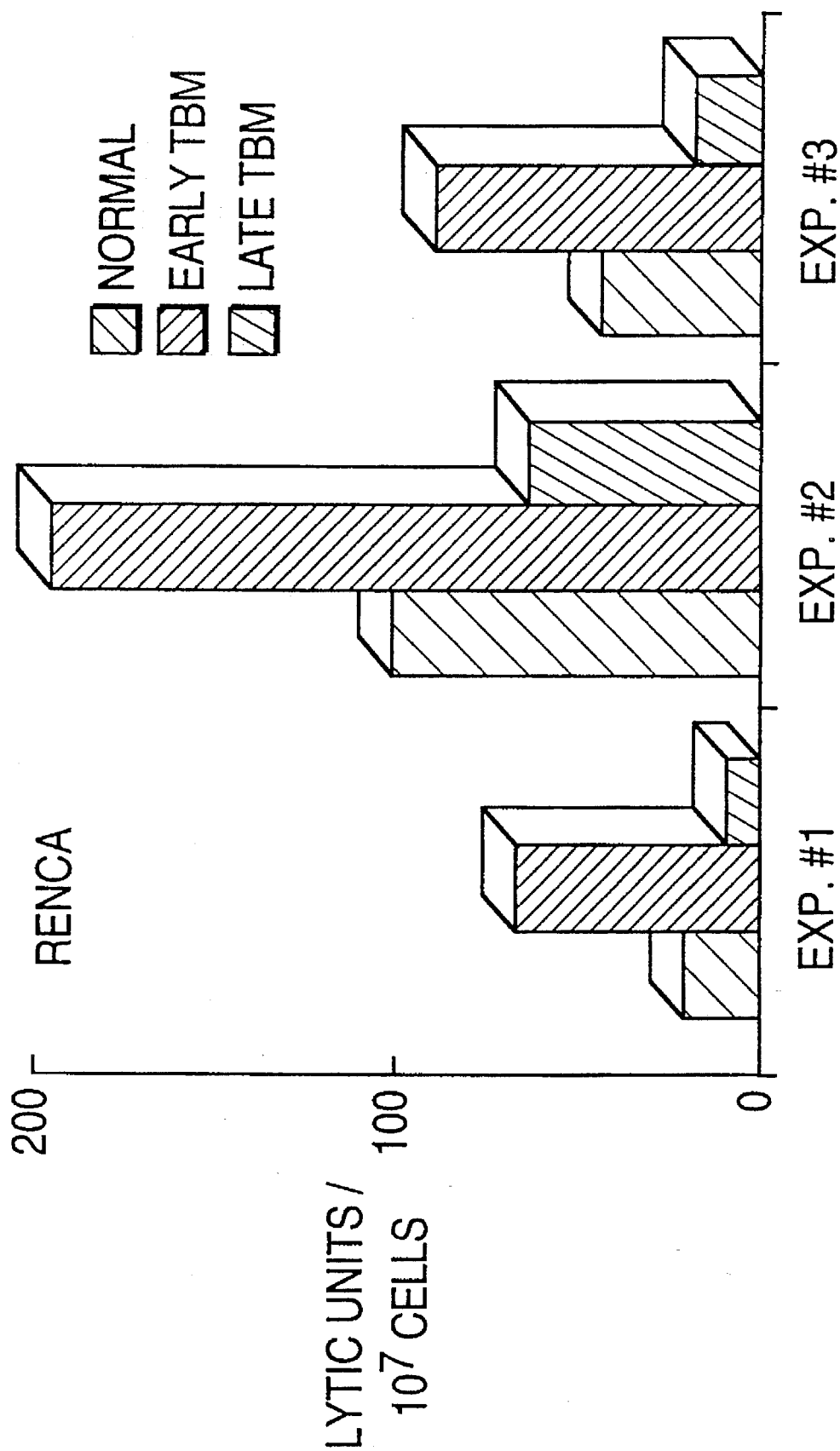

EVALUATION AND TREATMENT OF PATIENTS WITH PROGRESSIVE IMMUNOSUPPRESSION

This application is a continuation-in-part of U.S. Ser. No. 08/031,434, filed Mar. 15, 1993, now abandoned, which is a continuation-in-part of U.S. Ser. No. 07/987,966, filed Dec. 11, 1992, which is a continuation-in-part of U.S. Ser. No. 07/863,262, filed Apr. 6, 1992 and now U.S. Pat. No. 5,296,353.

BACKGROUND OF THE INVENTION

The invention relates a soluble immunosuppressive factor produced by cells of a tumor-bearing mammal and to a gene encoding said factor. Screening methods for agents inhibiting or reversing the action of this factor are identified. Immunosuppressive agents and counter-agents are recognized using the invention. The factor may be used to induce immunosuppression. The present invention also relates to the evaluation, selection and treatment of patients with diseases causing progressive immunosuppression. Patients having a disease responsive to immunotherapy, especially cancer patients, are staged or evaluated based on expression levels of proteins affected by immunosuppression. The likelihood of success of such immunotherapy is predicted by the results of staging and evaluation.

Many diseases are characterized by the development of progressive immunosuppression in a patient. The presence of an impaired immune response in patients with malignancies has been particularly well documented. Cancer patients and tumor-bearing mice have been shown to have a variety of altered immune functions such as a decrease in delayed type hypersensitivity, a decrease in lytic function and proliferative response of lymphocytes. S. Broder et al., *N. Engl. J. Med.*, 299:1281 (1978); E. M. Hersh et al., *N. Engl. J. Med.*, 273:1006 (1965); North and Burnauker, (1984).

Many other diseases are also characterized by the development of an impaired immune response. For example, progressive immunosuppression has been observed in patients with acquired immunodeficiency syndrome (AIDS), sepsis, leprosy, cytomegalovirus infections, malaria, and the like. The mechanisms responsible for the down-regulation of the immune response, however, remain to be elucidated.

The immune response is a complex phenomenon. T lymphocytes (T cells) are critical in the development of all cell-mediated immune reactions. Helper T cells control and modulate the development of immune responses. Cytotoxic T cells (killer T cells) are effector cells which play an important role in immune reactions against intracellular parasites and viruses by means of lysing infected target cells. Cytotoxic T cells have also been implicated in protecting the body from developing cancers through an immune surveillance mechanism. T suppressor cells block the induction and/or activity of T helper cells. T cells do not generally recognize free antigen, but recognize it on the surface of other cells. These other cells may be specialized antigen-presenting cells capable of stimulating T cell division or may be virally-infected cells within the body that become a target for cytotoxic T cells.

Cytotoxic or suppressor T cells usually recognize antigen in association with class I Major Histocompatibility Complex (MHC) products which are expressed on all nucleated cells. Helper T cells, and most T cells which proliferate in response to antigen in vitro, recognize antigen in association with class II MHC products. Class II products are expressed mostly on antigen-presenting cells and on some lymphocytes. T cells can be also divided into two major subpopulations on the basis of their cell membrane glycoproteins as defined with monoclonal antibodies. The $CD4^+$ subset which expresses a 62 kD glycoprotein usually recognizes antigen in the context of class II antigens, whereas the $CD8^+$ subset expresses a 76 Kd glycoprotein and is restricted to recognizing antigen in the context of Class I MHC.

The $CD4^+$ subset can be further subdivided into two functionally distinct groups. One group of cells positively influences the immune response of T cells and B cells. The second group of cells induces suppressor/cytotoxic functions in $CD8^+$ cells.

The definitive T cell marker is the T cell antigen receptor (TCR). TCR-2 is a heterodimer of two disulfide-linked polypeptides ($\alpha$ and $\beta$). TCR-1 is structurally similar to TCR-2, but consists of $\gamma$ and $\delta$ polypeptides. Both TCR-1 and TCR-2 are associated with a complex of polypeptides which comprise the CD3 complex.

The TCR found on the surface of all T cells is composed of at least six different subunits which can be divided into three distinct subgroups of proteins. R. D. Klausner et al., *Annu. Rev. Cell Biol.*, 6:403 (1990).

The Ti subunits are responsible for antigen binding, and include the $\alpha$, $\beta$, $\gamma$ and $\delta$ chains. The heterodimers $\alpha\beta$ or $\gamma\delta$ within the receptor complex are responsible for ligand binding. The $\alpha\beta$ heterodimer is found on most mature T cells and the $\gamma\delta$ heterodimer is found predominantly on T cells that are located in epithelia.

Another subgroup of proteins which comprise the TCR are the CD3 chains which encompass at least four distinct, but closely related subunits. These subunits are $\gamma$, $\delta$, $\epsilon$ and $\zeta$. F. Koning et al., *Eur. J. Immunology*, 20:299 (1990); R. S. Blumberg et al., *Proc. Natl. Acad. Sci. USA*, 87:7220 (1990). Diversification of receptor types is the result of segregation of chains of the TCR complex into multiple subunits. Incompletely assembled complexes are degraded, resulting in the surface expression of only completely assembled receptors. R. D. Klausner, *New Biol.*, 1:3 (1989).

In addition to the involvement of the TCR subunit proteins, T cell recognition events lead to signal transduction and appropriate biochemical signals that control cellular responses. The ability of TCR to transduce signals to multiple biochemical cascades is a central event of immune cell activation. The details of this signal transduction pathway, however, are poorly understood. For the TCR, one or more tyrosine (Tyr) kinases likely have an essential role in T cell activation. R. D. Klausner et al., *Cell*, 64:875 (1991). At least two signal transduction pathways are activated upon stimulation of TCR by an antigen or by monoclonal antibodies directed against either CD3 or the $\alpha\beta$ heterodimer.

Stimulation of TCR activates a tyrosine kinase. L. E. Samelson et al., *Cell*, 46:1083 (1986); M. D. Patel et al. *J. Biol. Chem.*, 262:5831 (1987); E. D. Hsi et al., *J. Biol. Chem.*, 264:10836 (1989). Phosphorylation of several proteins with tyrosine residues is induced within seconds of TCR stimulation. C. H. June et al., *J. Immunol.*, 144:1591 (1990). None of the TCR chains possesses intrinsic kinase activity. A member of the Src family of tyrosine kinases designated Fyn, however, coprecipitates with the CD3 complex. L. E. Samelson et al., *Proc. Natl. Acad. Sci. USA*, 87:4358 (1990). A T cell specific member of the Src family of tyrosine kinases, Lck, is tightly, but non-covalently, associated with the cytoplasmic domain of either a CD4 or CD8 molecule. The extracellular domains of CD4 and CD8 bind to MHC class II and class I molecules, respectively.

Upon binding of TCR to an antigen-MHC complex on a presenting cell, the TCR is believed to be brought into close proximity with either a CD4 or CD8 molecule that is capable of independently binding to an appropriate MHC molecule.

TCR also activates a phosphatidylinositol-specific phospholipase C which leads to hydrolysis of phosphatidylinositol-4,5-bis-phosphate. A. Weiss et al., *Proc. Natl. Acad. Sci. USA*, 81:4169 (1984); J. B. Imboden et al., *J. Exp. Med.*, 161:446 (1985). This leads to the liberation of two second messengers: 1) inositol-1,4,5-tris-phosphate which is responsible for transient $Ca^{2+}$ mobilization; and 2) diacylglycerol which is a potent activator of protein kinase C. B. Berridge et al., *Nature*, 341:197 (1989).

The cytoplasmic domain of the TCR ζ chain is sufficient to couple stimulation of the receptor with the signal transduction pathways. B. A. Irving et al., *Cell*, 64:891 (1991). When a chimeric protein linking the extracellular and transmembrane domains of CD8 to the cytoplasmic domain of the ζ chain was constructed, the chimeric protein activated the appropriate signal transduction pathways in the absence of CD3γ, δ, and ε. Therefore the role of ζ is apparently to couple the TCR to intracellular signal transduction mechanisms.

Another set of proteins that are related to signal transduction are the NF-κB/rel transcription factors. The NF-κB transcription activator is a multiprotein complex. The NF-κB transcription activator appears to have specialized in the organism to rapidly induce the synthesis of defense and signalling proteins upon exposure of cells to a wide variety of agents including cytokines, double-stranded RNA, T cell mitogens, DNA damaging agents, protein synthesis inhibitors, parasites, viruses and viral transactivators. A common denominator of the agents that activate NF-κB is that they either signal or represent a threat to cells and the organisms.

NF-κB is particularly suited to rapidly activate gene expression because (1) it does not require new protein synthesis, (ii) a simple dissociation reaction triggers activation, (iii) NF-κB actively participates in cytoplasmic-nuclear signalling and (iv) it is a potent transactivator.

NF-κB is involved in the inducible expression of the T cell growth factor interleukin-2 and a component of its high affinity receptor suggesting that NF-κB can be a growth regulator. There is indeed a good correlation between the proliferative state of T cells and the state of NF-κB activity.

Three protein subunits, $I_kB$, p50 and p65 control the biological functions of NF-κB. $I_kB$ is a 35–43 kDa subunit which inhibits the DNA-binding of NF-κB and serves to retain NF-κB in an inducible form in the cytoplasm of unstimulated cells. Upon stimulation of cells, $I_kB$ dissociates from the inactive complex with p65 and p50. The released p50–p65 complex heterodimer then migrates into the nucleus and trans-activates genes. Constitutive expression of the IL-2 receptor α gene in hybrids between a T-cell and myeloma cell line depends solely on the presence of the heterodimer. Only p65 appears to bind $I_kB$. Within cells, $I_kB$ could be released by modification of either $I_kB$, p65, or both.

Rel proteins are believed to be transcriptional activators, are capable of forming heterodimers with p50, and are sequence-specific DNA binding proteins which are capable of recognizing kB motifs. $I_kB$ is a member of a family of proteins that share homologies and apparently play a similar role in the cell. Both p50 and p65 have homologies to the rel and dorsal proteins. The $I_kB$ -family and rel-family therefore comprise related proteins which are known to be involved in cytoplasmic/nuclear signalling.

Other information on the NF-κB transcription activator and its relationship to the rel proteins may be found in Baeuerle, P. A. (1991), "The inducible transcription activator NF-κB regulation by distinct protein subunits", *Biophysica Acta* 1072:63–80.

Chemotherapy as a treatment modality has not been successful for all types of cancer. The identification and isolation of soluble mediators of the immune response has heightened interest in the development of clinical trials using immunotherapy as an alternative form of treatment. For example, biological response mediators (BRM) such as interleukin-2 (IL-2), a lymphokine produced by helper T cells, stimulates the growth of T cells that bear IL-2 receptors, either in vivo or in vitro. It also activates (enhances) the anti-tumor function of natural killers (NK) cells (Lotze et al. 1981). NK cells also express the ζ chain. The in vitro incubation of resting lymphocytes in supernatants containing IL-2 for three to four days results in the generation of lymphocytes capable of mediating the lysis of fresh tumor cells, but not of normal cells. These lysing cells are referred to as lymphokine activated killer (LAK) cells. I. Yron et al., *J. Immunol.*, 125:238 (1980); M. T. Lotze et al., *Cancer Res.*, 41:4420 (1981); and S. A. Rosenberg et al., *J. Natl. Cancer Inst.*, 75:595 (1985).

A method for the activation of T lymphocytes to generate T-activated killer cells (T-AK) has been described as taking lymphocytes by leukophoresis or from peripheral blood, and stimulating said cells with a monoclonal antibody (MAb) to a T cell surface receptor such as anti-CD3 (soluble or solid phase bound). The T cells can be stimulated with or without the addition of one or more cytokines such as IL-2. Alternatively, T cells can be purified before stimulation with the MAb to a surface receptor. Experimentation with T-AK cells has demonstrated that $CD8^+$ cells are responsible for the non-MHC restricted cytolytic activity seen in these cultures. P. M. Anderson et al., *J. Immunol.*, 142:1383 (1989); C. M. Loeffler et al., *Cancer Res.*, 51:2127 (1991). The ability of IL-2 to expand T lymphocytes having immune reactivity and the ability to lyse fresh autologous, syngeneic, or allogeneic natural killer (NK) cell-resistant tumor cells, but not normal cells, has resulted in the development of cell transfer therapies, such as autologous adoptive immunotherapy.

Typical adoptive immunotherapy involves the administration of immunologically active cells to an individual for the purpose of providing a beneficial immunological effect such as reduction or control of cancer. The immunologically active cells are typically taken by venipuncture or leukophoresis either from the individual to be treated, termed autologous treatment, or from another individual, termed an allogeneic treatment. The lymphocytes are then cultured to increase their number and to activate their antitumor activity, and then infused back into the patient. Thus, the majority of conventional efforts in adoptive immunotherapy are directed at expanding cell numbers in vitro followed by infusion back into the patient.

Animal experiments involving the transfer of immunologically active cells from healthy animals to animals with cancerous tumors have indicated that adoptive immunotherapy can elicit an antitumor effect in certain tumor models with a high degree of effectiveness. The administration of IL-2 together with LAK cells has proven effective in the treatment of a variety of murine malignancies. The transferred LAK cells also proliferate in vivo as a result of IL-2 treatment. Human clinical trials have demonstrated that LAK cells plus IL-2 or IL-2 alone can be effective in mediating the regression of established metastatic cancer in selected patients. S. A. Rosenberg, "Immunotherapy of Patients with Advanced Cancer Using Interleukin-2 Alone or in Combination With Lymphokine Activated Killer Cells,"

in *Important Advances in Oncology* 1988: J. B. Lippincott Co., 217, (1988).

However, the success of adoptive immunotherapy has been limited by the large number of cells required in the therapy, the large amount of culture medium and large number of hours involved in culturing cells to develop LAK activity, the length of time sufficient LAK activity must be maintained for the desired therapeutic efficacy, the time involved in clinical treatment and the side effects of treatment. Improvements in the in vitro culturing process have been sought in order to increase the efficacy of adoptive immunotherapy. Cells cultured in IL-2 and/or monoclonal antibodies against the antigen receptor complex CD3 (anti-CD3 MAb) have been found to induce proliferation of a greater number of T cells, which demonstrate an increased anti-tumor activity. P. M. Anderson et al. *Cancer Immunol. Immunother.*, 27:82 (1988); P. M. Anderson et al., *J. Immunol.*, 142:1383 (1989); and A. C. Ochoa et al., *Cancer Res.*, 49:963 (1989).

Adoptive immunotherapy of renal adenocarcinoma in the murine RENCA model using IL-2-activated killer cells in conjunction with chemotherapy showed some success in reducing tumors, but the effect was suspected to be cytokine mediated. Wiltrout, *Progress in Neuro Endocrin Immunology*, 4:154 (1991).

There has been limited success with efforts to activate in vivo antitumor mechanisms. Only a minority of patients receiving high doses of IL-2 experienced therapeutic effects, and significant toxicity is observed. The direct infusion of anti-CD3 monoclonal antibody alone inhibits nonspecific antitumor function in mice. D. W. Hoskin et al., *Cancer Immunol Immunother.*, 29:226 (1989). Based on the positive results in murine models, direct infusion of anti-CD3 has been attempted in humans. Although patients who have directly received the anti-CD3 MAb designated OKT3 have experienced the activation of some T cells in vivo, the toxicity of intravenous OKT3 reaches the maximum tolerated dose (MTD) at low doses before it starts showing some immune efficacy. W. Urba et al., *Cancer Res., Cancer Res.* March 1991. It is believed that the free OKT3 is responsible for the majority of these toxic effects.

Due to inadequacies of treatment with single modalities, synergism has been sought. Flavone acetic acid (FAA) is a cytokine-inducing synthetic drug which showed a synergistic therapeutic effect with IL-2 in reducing RENCA murine tumors. Antitumor effects of flavonoids and cytokines in combination with IL-2 are therefore promising. FAA is a biological response modifier (BRM) which has been shown to augment systemic natural killer (NK) cell activity and to synergize with IL-2 for the successful treatment of advanced RENCA. Wiltrout et al., *J. Immunol.*, 140:3261 (1988); U.S. Pat. No. 5,096,707 and 5,061,488. Cytokines (TNF, α-IFN, and γ-IFN) induced by FAA have been implicated in the therapeutic synergy with rIL-2. $CD8^+$ T-lymphocytes are critical in mediating this synergistic effect. FAA induces cytokine genes in vitro. In this model, immunosuppressive T-cells are induced during the progression of the RENCA tumor. Gregarian et al., *Cancer Immunol Immunother* 31:325, 31:335 (1990).

T lymphocytes from hosts bearing tumors exhibit decreased immune function in a variety of in vitro tests. R. Lafreniere et al., *J. Surg. Oncol.*, 43:8 (1990); R. J. North et al., *J. Exp. Med.*, 159:1295 (1984); M. Sarzotti et al, *Int. J. Cancer*, 39:118 (1987). It has been observed that before the decrease in the immune responsiveness in peripheral blood lymphocytes, T lymphocytes infiltrating a tumor exhibit poor cytotoxic activity against autologous or allogeneic tumor cells. E. F. Klein et al., 1980, In: *Contemporary Topics in Immunobiology*, I. P. Witz and M. G. Hanna, Jr., eds. Plenum Press, N.Y., p 79–107; B. M. Vose et al., *J. Cancer*, 44:846 (1981).

The molecular basis of the decreased immune responsiveness of the T cells derived from tumor-bearing hosts is poorly understood. It has been proposed that decreased immune responsiveness of the T cells is caused by the development of suppressor lymphocytes. S. B. Mizel et al., *Proc. Natl. Acad. Sci. USA*, 77:2205 (1980); C. C. Ting et al., *Int. J. Cancer*, 24:644 (1979). Another proposal is that responsive T cell clones are deleted. S. Webb et al., *Cell*, 63:1249 (1990). It has also been proposed that decreased immune responsiveness of the T cells is the result of the induction of T cell anergy. M. K. Jenkins et al., *J. Exp. Med.*, 165:302 (1987). Others have suggested that the major alteration in the immune response is produced by a modification in the presentation of the antigen which results in an inadequate response of the $CD4^+$ helper T lymphocytes. These data have been strengthened by the observation that tumor cells transfected with cytokine genes induce a protective antitumor response, and result in an immunological memory response. E. R. Fearon et al., *Cell*, 60:397 (1990).

In an in vivo tumor model, the progressive growth (>26 days) of a subcutaneous implant of murine colon carcinoma designated MCA-38 resulted in decreased lytic function by the $CD8^+$ T lymphocytes, a decrease which was associated with decreased expression of mRNA for tumor necrosis factor α (TNF-α) and granzyme B, and the complete loss of the ability of adoptively transferred cells to mediate an antitumor effect in vivo (Loeffler et al. 1992, *J. Immunol.*149:949). However, proliferation, lymphokine production, and lymphokine receptor upregulation in $CD4^+$ T cells were comparable in normal and tumor-bearing mice. Cells with suppressor function were not detected, nor was the production of transforming growth factor-β (TGF-B) detected in the lymphocytes from tumor-bearing mice or the MCA-38 tumor cells.

Augmentation of the immune response in immune compromised patients via infusions of lymphokines and/or adoptive immunotherapy has met with variable and limited success. Methods are needed to improve this type of treatment. A need exists for effective methods of measuring the progression of immunosuppression so that attempts at augmenting the immune system in an immunosuppressed patient can be effectively timed. A need also exists for a method by which a patient's level of immunosuppression is estimated and used to accurately predict the likelihood of a patient's response to therapy. The patient's therapy can then be developed in a systematic fashion. A method is needed by which a clinician can determine whether a patient's T lymphocytes will be capable of activation and, thus, whether autologous adoptive immunotherapy will likely be efficacious.

A need exists for a method by which the immunosuppressed state of T lymphocytes during disease progression can be circumvented or reversed so that the T cell immune response in the patient can develop or be augmented. A need also continues to exist for a method of screening for immunosuppressive agents and agents that reverse or inhibit immunosuppression.

There is a need to detect the presence of tumors, in particular early in the development of a tumor, so that treatment effectiveness is enhanced. Also, improved methods for staging of the disease would facilitate choice of the most appropriate treatment modalities. There is also a need to test the effectiveness of treatment modalities prior to clinical trials, and as adjuncts to clinical trials.

The present invention addresses limitations in the art for the detection, monitoring, and reversal of immunosuppression, and of diseases generally characterized by immunosuppression, for example, cancer.

SUMMARY OF THE INVENTION

The present invention relates to identification of a soluble immunosuppressive factor which is capable of effecting a change in the level of various proteins involved in the TCR subunits, in the T lymphocyte signal transduction pathway, and in the pattern of the NF-κB/rel proteins.

By "factor" is meant a composition that is present in the serum derived from an immunosuppressed mammal and is capable of altering the expression of the TCR related proteins. The factor is present in the supernatant of some tumor cell cultures. The term "factor" includes any subcomponent that is isolated and purified from said serum or supernatant, and has the immunosuppressive and TCR protein altering properties described herein. The change in the level of protein expression may occur in one or more proteins that compromise the TCR receptor, the T lymphocyte signal transduction pathway, and the NF-κB/rel proteins.

The level of expression of specific proteins that comprise the TCR receptor and specific proteins in the signal transduction pathway, is generally decreased in immunosuppressed mammals as compared with the level characteristic for the proteins in a preparation of cells derived from a non-immunosuppressed mammal, or from a culture of cells which originated from a non-immunosuppressed mammal, or a culture of cells characterized by a protein level characteristic of a non-immunosuppressed mammal. However, because expression of the proteins that are an aspect of the present invention are part of an inter-related and complex immunological system, a perturbation in one protein of the system may effect other protein levels in different ways, that is, may either increase or decrease them at a particular point in time.

What is important is that if at least one protein level in the immunological system is decreased to a level which disrupts the operation of the system, the system becomes suppressed, that is, unable to operate as is necessary to perform the immunological functions characteristic of a healthy mammal. The degree of suppression varies, and is generally associated with more severe clinical problems as suppression becomes more pronounced. Also, as immunosuppression progresses, more protein levels tend to show changes. As an indicator of the progression of immunosuppression, the level of a particular protein decreases correspondingly, and a plurality of proteins of the present invention show alterations from the non-immunosuppressed state. Generally the protein levels decrease, although some levels increase. For example, as CD3ζ decreases, FCεγ increases.

An embodiment of a protein which decreases in the presence of the immunosuppressive factor of the present invention is a protein subunit of TCR. These proteins include CD3ζ and CD3γ.

An embodiment of a protein which increases as the CD3ζ level decreases, that is, whose expression is inversely correlated with the expression of this protein, is Fcεγ, a protein related to the IgE receptor. Control of the Fcεγ protein by methods of the present invention may represent a way to control an allergic response because the methods of the present invention are useful for screening for increased FCεγ and for selecting agents to inhibit that increase.

Another embodiment of a protein which decreases in the presence of the immunosuppressive factor is a signal transduction pathway protein. This protein includes a tyrosine kinase such as those of the Src family, notably Fyn and lck, as well as proteins PLCγ and GAP.

The pattern of protein transcription factors in the NF-κB/rel system is altered in the presence of tumors, a condition associated with the immunosuppressive state. A pattern in this context refers to the presence or absence of different protein components of the NF-κB/rel family which are found in the non-immunosuppressed state in non-tumor bearing mammals, and to the presence or absence of various related components characterized by physical properties such as molecular weight which are different from the properties in the non-immunosuppressed, non-tumor bearing, state. The presence or absence of the NF-κB/rel factors, and their physical properties such as molecular weight, are determined by methods known to those of skill in the art. These methods include Western blot analysis, gel shift analysis, and UV-crosslinking analysis. Nuclear extracts are analyzed. If lymphocyte preparations are used for the assay, for example from a spleen, short term cultures are preferred.

Other properties of the soluble immunosuppressive factor of the present invention include its presence in the serum of mammals that have tumors present. It also appears in the supernatant of cultures of some tumor cells.

It was found that supernatants of some cultured tumor cells suppressed the in vitro cytolytic activity of normal lymphocytes. Embodiments of said cultures include MCA-38 and MBL-2. The factor may, therefore, be isolated and purified from preparations of mammalian cells derived from tumor-bearing sources. The factor is recoverable after a certain period of time that the tumor has been present in the mammal. The longer the tumor is present, the more likely is the factor to be recoverable. It is understood that there may be one or more tumors. The period after which the factor is recoverable varies with the type of mammal, the type of tumor, and other factors related to the malignant state. For example, the soluble factor is recoverable from mice that have tumors present for at least about 26 days in the tumor lines disclosed herein.

The soluble factor is recoverable from biological specimens that include mammalian serum. The factor is also recoverable from the supernatant of some cultured cells, for example, cells cultured from the MCA-38 line or from the MBL-2 lymphoma line. These lines are available for use as described herein.

A general method for determining the level of immunosuppression in a mammal, includes the steps of determining the level of expression, in a mammalian lymphocyte preparation, of at least one selected TCR subunit protein or protein in the T lymphocyte signal transduction pathway; and comparing the level of protein expression with the characteristic level of expression of the selected protein found in healthy, that is, non-immunosuppressed, individuals of the same mammalian species. The TCR subunit proteins that are suitable for the practice of the present invention include CD3ζ or CD3γ. The proteins in the signal transduction pathway that are suitable for the practice of the present invention include tyrosine kinases of the src family $p56^{lck}$ and $p59^{fyn}$, and the proteins PLCγ and GAP.

Embodiments of changes in levels of protein expression which are directly associated with progression from the normal to the malignant state include: T cell antigen receptors (TCR) that show decreases in CD3γ and a complete lack of a CD3ζ chain. The latter chain is replaced by an Fcεγ-chain.

Embodiments of changes in the levels of expression of proteins in the lymphocyte signal transduction pathway that are associated with progression from the normal to the malignant state included reduced expression of tyrosine kinases. In an illustrative embodiment, $p56^{lck}$, $p59^{fyn}$, PLCγ and GAP are reduced compared to normal levels. In any one individual, one or more protein levels may be changed. As malignancy progresses, generally, more protein levels are changed. The sequence of appearance of the changes may vary with different diseases.

Changes discovered herein are observed both in tumor-bearing mice and humans when compared to non-tumor-bearing animals or humans. At least one change from normal TCR complex protein expression level is observed, although generally there is a correlated response, that is, a pattern associated with the advancing malignant state.

Another assay for the immunosuppressed or tumor-bearing state is the pattern of the transcription factors of the NF-κB/rel family. The proteins of interest include c-rel, p65 and p50. In some abnormal conditions, all three proteins are absent. In other conditions, only one or two are absent. In still other abnormal conditions, new forms of protein replace a form present in the normal state. Comparisons are preferably made between comparable cell samples from a mammalian species. For example, in the presence of a RENCA tumor in a mouse, p50, a component of nuclei of a T lymphocyte preparation from a non-tumor bearing mammal, disappears, and is replaced by p48 and p44 ( proteins with estimated molecular weights of 48 and 44 kD respectively as determined by Western blots.) Some of the new protein forms appear to be related to the larger molecular weight form they replace, by N-terminal truncation of the larger form.

Cancer patients are staged or evaluated based on expression levels and patterns of proteins affected by immunosuppression. The likelihood of success of such immunotherapy is predicted by the results of staging and evaluation. The protein levels of the TCR subunits and signal transduction pathway, and the pattern of the NF-κB/rel proteins, are informative for these purposes. In vitro responses of cells to therapies may be predictive of either the efficacy of the treatment, or the immunological strength of the cells, or a correlate thereof.

An aspect of the present invention is that it provides a method of identifying a patient having T lymphocytes capable of activation for autologous adoptive immunotherapy by assaying for changes in TCR receptor, signal transduction, or NF-κB/rel proteins. This method includes the steps of determining, in a lymphocyte preparation from a patient being evaluated for immunosuppression, the level of expression of at least one selected TCR subunit protein or of a protein in the T lymphocyte signal transduction pathway, or the pattern of at least one of the NF-κB/rel proteins.

A method for quantitating the level of expression of the proteins of the present invention is the expression ratio, although other comparable methods are within the scope of this invention. An expression ratio is the ratio of the number of T lymphocytes expressing the selected protein to the total number of T lymphocytes counted. The level of protein expression is compared with the normal level of expression of the selected protein found in healthy, that is, non-immunosuppressed individuals. Another method for quantitating an expression level of a protein of the present invention is to express the amount (proportion) of the protein present in an amount of total protein isolated from a biological specimen, e.g. T-lymphocytes.

For the pattern of transcription factors of the NF-κB/rel family, presence or absence of molecular weight components are determined in nuclear extracts. At least one component is assayed, although preferably a plurality are assayed, because different abnormal states are characterized by different patterns.

A threshold is defined as a level which is the minimum level of a protein which is compatible with lymphocyte stimulation. A threshold may also be defined as a pattern of NF-κB/rel proteins that is compatible with lymphocyte stimulation. Compatibility is determined as that level of stimulation effected by agents such as anti-CD3 that is generally required for clinical improvement, in therapies involving lymphocyte transfusions. Alternatively, a threshold level is defined as a protein level and/or pattern that does not interfere with the immunological response.

Application of the methods of the present invention to the treatment of patients having a disease responsive to immunotherapy, permits selection of patients whose lymphocytes are likely to respond to stimulation, and for whom immunotherapy is likely to succeed. Patients whose level of expression of a selected protein or proteins, and/or pattern of proteins, is not below the threshold level for response to lymphocyte stimulation, are likely candidates for immunotherapy.

Another aspect of the present invention relates to a method of selecting agents which cause immunosuppresion of mammalian T lymphocytes. The method includes the steps of: providing a mammalian T lymphocyte preparation wherein the level of expression of at least one selected TCR subunit protein or protein in the signal transduction pathway, and/or pattern of NF-κB/rel proteins, is characteristic of healthy, that is, non-immunosuppressed, individuals of the same mammalian species; culturing the lymphocyte preparation in the presence of an agent suspected of causing immunosuppression; determining the level of expression and/or pattern of the selected protein; and selecting an agent which causes a significant reduction below normal in the level of expression of the selected protein, or a pattern change from normal, wherein normal is defined as a threshold level determined to represent the non-immunosuppressed state. This process is conducted in vivo after the administration of a potentially immunosuppressive drug. A method of inducing immunosuppression, for example, in conjunction with organ transplantation, is to administer the soluble immunosuppressive factor of the present invention to a patient.

Similarly, a method of identifying an agent which reverses immunosuppression of mammalian T lymphocytes, includes the steps of: providing a mammalian T lymphocyte preparation from an immunosuppressed mammal, wherein the level of expression of at least one selected TCR subunit protein or protein in the signal transduction pathway is below that threshold level characteristic of healthy i.e. non-immunosuppressed individuals of the same mammalian species, or exhibits an altered pattern of NF-κB/rel proteins, or some combination of either type of changes; culturing the lymphocyte preparation in the presence of an agent suspected of reversing immunosuppression; determining the level of expression of the selected protein; and selecting for an agent which causes a significant increase in the level of expression of the selected protein. This process is conducted in vivo after the administration of a drug that potentially reverses immunosuppression.

Using the methods of the present invention to detect changes in proteins of the TCR subunits, the signal transduction pathways, or the NF-κB/rel proteins, treatments to reduce or eliminate tumors, may be evaluated. For this evaluation, levels of the proteins are determined in a tumor bearing mammal prior to administering the treatment. Following treatment, the levels or patterns or both, of the same proteins are determined and compared to pre-treatment levels to determine whether changes have occurred. Generally, statistically significant differences are required to decide that changes have occurred. Comparisons may also be made to protein levels of comparable non-tumor-bearing mammals for further evaluations of treatment efficacy.

In an illustrative embodiment, mammals bearing established tumors are treated with a combination of a flavonoid and a cytokine in conjunction with IL-2. Evaluation of alternations in the tyrosine phosphorylation pattern indicates that reduced levels of $p56^{pck}$, $p59^{fyn}$ PLCγl and the zeta chain of the CD3-complex associated with presence of a tumor, are reversed after said treatment in mice that also show tumor reduction. c-rel and p65 of the NF-κB/rel family were absent, and p48 and p44 appeared in place of p50. An interpretation of these results is that the flavonoid, cytokine, IL-2 combination, acts against tumors by restoring the components required for normal immunological functioning, for example, signal transduction pathways, thereby allowing the T-cells to mount an effective anti-tumor response.

Embodiments of agents that induce re-expression of the CD3ζ protein after its level has been decreased in tumor-bearing mammals, include: ionomycin; ionomycin in combination with any of the following: phorbol miristic acetate, IL-2, PMA and IL-2, anti-CD3 and IL-2; and the monoclonal antibody, anti-CD3.

A screening method for an agent that inhibits the immunosuppressive factor of the present invention is performed by determining the immunosuppression level of a system to which the agent has been added, and comparing the level to the immunosuppression levels before adding the agent. An illustrative embodiment includes the following steps:

1. developing a monoclonal antibody to the agent so that a complex will be formed when the antibody is added to a preparation containing the agent, thereby inhibiting the action of the agent; the antigen-antibody complex is labelled by methods know to those of skill in the art to detect its formation, thereby leading to the inference that the agent is present in a preparation;

2. adding the agent to be tested to a first cellular system that contains the immunosuppressive factor;

3. adding both the agent and the antibody directed to the agent, to a second cellular system that also contains the immunosuppressive factor;

4. determining the level of immunosuppression using the assays of the present invention to determine protein expression levels, for example of the TCR subunits and the signal transduction pathway, and/or the pattern of the NF-κB/rel proteins;

5. comparing the immunosuppression levels of the first cellular system with that of the second to determine whether the monoclonal-antibody containing system exhibits a reversal of immunosuppression; this reversal is indicated by the protein levels and/or patterns of the second cellular system being above the levels of the first cellular system, and preferably, the levels or patterns being consistent with levels or patterns characteristic of the non-immunosuppressed state of a comparable cellular system; a comparable cellular system includes a system derived from the same mammalian species, the same cell type, and having other immunologically related properties that are similar.

This invention also relates to an agent identified by the methods of the present invention as inhibiting the immunosuppressive factor, that is, preventing or reversing immunosuppression effected by a malignant state or other abnormal conditions which induce immunosuppression. Immunosuppression caused by chemical modalities are included in this definition.

An antibody directed to the immunosuppressive factor is also within the scope of the present invention. The antibody is prepared by employing an isolated and purified epitope of the isolated immunosuppressive factor of the present invention by methods known to those of skill in the art for preparing polyclonal and monoclonal antibodies.

An immunosuppressive factor is isolated and purified from serum of tumor-bearing mammals, from cells that are derived from tumors or tumor-bearing mammals, or from other biological sources that effect immunosuppression when applied to non-immunosuppressed systems. In an illustrative embodiment, the factor is a soluble proteinaceous compound. Using the isolated and purified factor, the gene or genes encoding the immunosuppressive factor are cloned and the nucleotide coding sequences determined.

A gene encoding the immunosuppressive factor of the present invention is cloned by methods known to those of skill in the art. The factor, or at least the segment necessary for immunosuppression, may be purified by use of a monoclonal antibody directed against the factor or epitopic segments thereof or by standard biochemical purification. The amino acid sequence is determined for the purified factor and degenerate oligonucleotides are prepared and used to screen a library of nucleotide sequences.

An antisense construct directed against the expression of the immunosuppressive factor of the present invention is useful for inhibiting the action of the factor. Administration of the antisense construct to a mammal is used to inhibit progression toward the immunosuppressive state. The antisense construct is generally transfected into cells, and the cells administered to a mammal.

Mammalian cells may be transfected with the gene for the soluble factor using methods known to those of skill in the art.

An aspect of the present invention is a vaccine which is prepared from at least an immunologically active portion of the soluble immunosuppressive factor of the present invention. The vaccine is prepared by methods known to those of skill in the art.

A kit for determining the level of immunosuppression includes an antibody directed to a protein from a group including a TCR subunit, a signal transduction pathway, and a NF-κB/rel family. In separate containers, one or more antibodies are present, each directed to an individual protein of the present invention, also included in the kit are means for detecting the formation of an antigen-antibody complex, from which the presence of a particular protein is inferred. An antibody specific for the sequence that differs in an abnormal compared to a normal state, is useful for detecting degraded proteins.

A kit for determining effectiveness of therapeutic agents for reversing immunosuppression and tumor progression, includes several lymphocyte preparations each in a separate container. A first preparation is provided for control levels and patterns. This is generally a lymphocyte preparation from a spleen of a non-immunocompromised, non-tumorbearing mammal of the same species as the mammal for which the therapy is directed. A second preparation of comparable cells and mammalian source is from an immunosuppressed or tumor-bearing mammal. Generally, the cells are required to be frozen in liquid nitrogen upon receipt of the kit, until the kit is to be used. The preparations will either be nuclear extracts, or the kit will include lysing means to provide nuclei for the analysis of the NF-κB/rel patterns. The efficacy of the potential therapeutic agent is determined by adding the agent to the second preparation, and comparing protein levels and/or patterns by methods known to those of skill in the art, after an appropriate interval. The appropriate interval is determined for a particular cell type, and protein assay.

Mammalian cells treated with an agent that inhibits the immunosuppressive factor, and mammalian cells treated with the immunosuppressive factor, are useful therapeutically for either decreasing or increasing immunosuppression, depending on the nature of the disease or condition to be treated. The treated cells may be used for adoptive immunotherapy.

An immunosuppressed mammal is treated by administering a therapeutically effective amount of an agent identified by the methods of the present invention as capable of reversing immunosuppression, in a pharmaceutically acceptable diluent. Therapeutically effective amounts are determined empirically for a particular disease or condition. The treated mammal includes a human.

Further objects, features and advantages of the invention will become apparent from the detailed description of the invention which follows, in which various terms used are defined as follows:

T lymphocytes or T cells include all subsets of lymphocytes which carry the T cell antigen receptor. These subsets include lymphocytes which are $CD3^+CD4^+(\alpha\beta^+)$; $CD3^+CD8^+(\alpha\beta^+)$; $CD3^+CD4^-CD8^-(\gamma\delta^+)$; and $CD3^+CD56^+$.

Immunotherapy includes adoptive immunotherapy which includes cellular adoptive immunotherapy which involves the administration of immunologically active (immunocompetent) cells to an individual for the purpose of providing a beneficial immunological effect to the individual, such as reduction or control of cancerous or diseased tissue.

As used herein, immunotherapeutic activity or immune response or immunologically active or immunocompetent includes anti-tumor activity, anti-infected cell activity, anti-disease agent activity and killer activity of white blood cells.

Culturing indicates the process whereby T cells are placed in a tissue culture medium (TCM) comprising all the nutrients required for growth. Stimulating indicates culturing the T cells in a TCM supplemented with one or more cytokines, or alternatively, with one or more T cell anti-surface receptor antibodies, with or without one or more cytokines. The process can take place in any vessel or apparatus suitable for cell or tissue culture. The process can involve various stages of culturing and subculturing. However, typically only one stimulating step is desirable.

The signal transduction pathway includes any protein, the expression of which is induced, linked or regulated by the binding of a ligand or an antibody to any T cell surface receptor. These proteins include, but are not limited to, Jun, Fos, Myc, GAP, Raf1, c-rel, NF-κB, Plcγ, Protein G, Inositol Phosphate, Protein Kinase C, Map1-kinase, CD45 phosphatase and the Src family of kinases including Lck, Fyn, Yes and Lyn.

Antibody includes any protein or protein analogue which binds specifically to an appropriate epitope of the T cell receptor that is stimulatory. Antibody also includes any protein or protein analogue which binds specifically to a TCR subunit protein, Fcεγ, or a protein in the T lymphocyte signal transduction pathway. The term includes antibodies made by conventional methods including polyclonals, monoclonals or fragments thereof, as well as genetically engineered or synthetic molecules, e.g., single chain antibodies, that contain a binding region that is the functional equivalent of an antibody in its binding specificity.

Cytokine includes those proteins which mediate much of the intercellular signalling required for an integrated response to a variety of external stimuli. Cytokines are potent mediators which interact with specific high affinity receptors on the cell surface. Cytokines have been shown to affect the function of all cell types involved in an immune response; to be involved in lymphopoiesis and hemopoiesis; and have been implicated in the pathophysiology of a large number of diseases. Lymphokines are the preferred cytokines in the claimed invention.

NF-κB transcription activator is a multiprotein complex which activates gene transcription. Three protein subunits, $I_kB$, p50 and p65 control the biological functions of NF-κB. Rel proteins are transcriptional activators, are capable of forming heterodimers with p50, and are sequence specific DNA binding proteins which are capable of recognizing kB motifs.

DESCRIPTION OF THE PREFERRED EMBODIMENT

Figure 1:
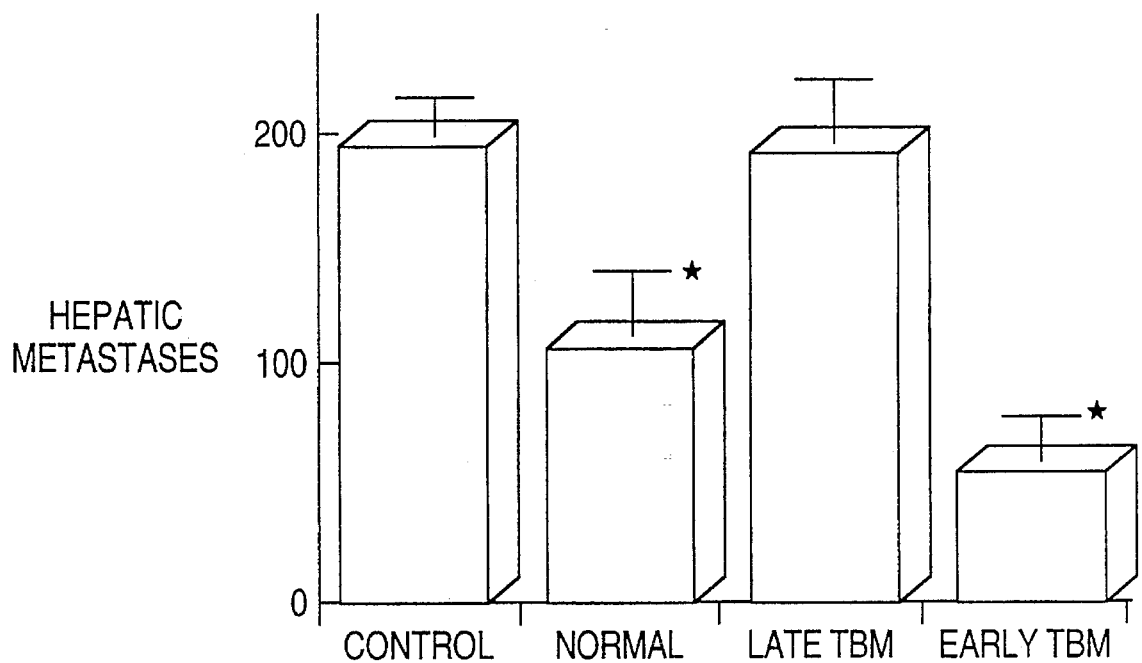
FIG. 1 illustrates the results of an experiment in which mice were treated with T-AK cells derived from three groups of mice: (1) non-tumor-bearing mice (normal), (2) mice bearing a tumor for <21 days (early TBM); (3) mice bearing a tumor for >30 days (late TBM). Liver metastases were counted 12 days after tumor inoculation. Groups were compared using Student's unpaired t test. *indicates a P<0.001, treated versus control; Bars show the S.D. (standard deviation).

T-lymphocytes from tumor-bearing mice (TBM) in particular those having tumors for a long period of time, show alterations in the characteristics of the TCR related proteins.

Cancer patients show similar alterations. These observations suggest that proliferation of tumors relate to break-down in operation of proteins of the TCR subunits, the signal transduction pathways, and the NF-κB/rel system. Conversely, successful anti-tumor therapy correlates with reversal of alterations in these proteins, for example, reversal from the lack of, or diminished expression of, these proteins, to their presence at normal levels.

These observations provided the basis for developing assays for immunosuppression in mammals. The assays are based on changes in the TCR subunit proteins, in proteins of the signal transduction pathway, and in the NF-κB/rel system. Clinical uses for these assays are numerous.

A soluble immunosuppressive factor present in tumor bearing mammals was identified by its effect on the TCR related proteins of the present invention and by its association with progressive immunosuppression.

The methods of the present invention are suitable for the evaluation of treatments, and to methods of treatments of a great variety of diseases characterized by the malfunctioning of the immune system. Such diseases include those that result in progressive immunosuppression as well as diseases in which "self" is recognized as foreign and therefore, an autoimmune response is established.

Diseases which result in progressive immunosuppression include cancers of many different tissues including leukemia, Hodgkin's disease, lung cancer, colon cancer, gliomas, renal cell carcinoma, and the like. Progressive immunosuppression is observed in a great variety of infections including those that are intracellular such as leprosy, tuberculosis, leishmania; those that are extracellular such as sepsis, diseases of viral etiology such as those caused by HIV, cytomegalovirus, Epstein Barr, and the like; parasitic infections such as schistosomiasis, malaria, and the like.

Diseases which result in the establishment of an autoimmune response include lupus, autoimmune thyroiditis, scleroderma, rheumatoid diseases such as rheumatoid arthritis, and the like.

Organ transplantation requires induction of immunosuppression. The soluble factor of the present invention is useful to achieve this state. The assays of the present invention are used to evaluate immunosuppressive agents.

Treatment modalities are developed from identification of immunosuppressive agents or agents that reverse immunosuppression, by assays of the present invention. Treatments include direct administration of immunological stimulants to a mammal having cancer or another disease impairing the immune system, or use of adoptive immunotherapy.

A method of delivery of effective immunotherapeutic agents are liposomes. Effective immunotherapeutic agents include those that restore levels of TCR subunits and signal transduction proteins, to levels prior to the appearance of tumors, or prior to induction of the diseased state. Effective immunotherapeutic agents include those that restore the transcriptional factors of the NF-κB/rel family to their prediseased state.

Characteristics of T-Lymphocytes from (TBM) Tumor-Bearing Mice

1. Decrease in Therapeutic Efficacy

There was a marked decrease in the therapeutic efficacy of adoptively transferred T lymphocytes from murine hosts bearing a tumor for >26 days (These hosts are referred to as late tumor-bearing mice or late TBM) as distinguished from normal mice and mice bearing a tumor for <21 days (early tumor-bearing mice or early TBM).

In vitro analysis of the functions of the T lymphocytes from late TBM showed an apparently normal proliferative response to anti-CD3 and IL-2 and adequate lymphokine production from $CD4^+$ cells. However, a significant decrease in the cytotoxic function of $CD8^{3o}$ cells, was observed. The decreased cytotoxicity was not due to cell-mediated suppression. The expression of genes encoding for lytic molecules such as TNFα and granzyme B was significantly decreased.

Expression of the CD3ζ and CD3ζ chains was not detectable in T lymphocytes from late TBM. The ζ chain was replaced by the expression of the Fcεγ chain, a member of the ζ family of chains. Lymphocytes from TBM also exhibited a marked decrease in the Lck and Fyn proteins. These changes were paralleled by a decreased ability to mobilize $Ca^{2+}$ and in an altered pattern of tyrosine phosphorylation.

$CD8^+$ T lymphocytes in tumor-bearing mice have impaired lytic and therapeutic function (Loeffler et al., 1992) and alterations in the expression and function of signalling molecules. CD3ζ-chain is not only a critical signal transducing component of the TCR (Romeo and Seed, Cell 64, 1037, 1991), but also the limiting subunit in the assembly and membrane expression of the TCR-CD3 complex in T cell hybridomas. Weissman et al., Science 239:1018, 1988). Lytic function is reduced in cells lacking the TCR-α-chain or the CD3-δ-chain. Schmitt, Verhuisi et al., Nature 325:628 (1987). The effect of the absence of either CD3ζ or CD3γ from T cells in tumor-bearing mice is not clear.

A subpopulation of large granular T-lymphocytes (LGLs) characterized as $CD3^+$, $NK1.1^+$, $CD16^+$, $CD4^-$, and $CD8^-$ and expressing the Fcεγ-chain instead of the ζ-chain has been described (Koyasu, J. Exp. Med. 175:203, 1992). These lymphocytes differ phenotypically from those seen in tumor-bearing mice. However, these LGLs do have lytic function. Thus, target cell lysis is not dependent on the presence of the CD3ζ-chain. Moreover, chimeric molecules made with Fcεγ expressed in cytotoxic T cell lines maintain their lytic function. This suggests that Fcεγ and ζ may be interchangeable in coupling to lytic mechanisms, especially in view of the degree of homology between these two chains (Romeo et al., Cell 68:899 (1992).

2. Decreased Expression of PLC γ and GAP Tumor Bearing Mammals

Experimental data using a Western blot technique and using the antibody against PLC-γ (Upstate Biotechnologies Inc., Lake Placid, N.Y., 1:5000 dilution) and anti-GAP (same company, at 1:2000 dilution) has demonstrated a decreased expression of both antigens in tumor-bearing mice. Testing of these signal transduction mediators in cancer patients has shown a decrease in PLC-γ, but not always in GAP.

3. Decreased Kinase Function in Tumor Bearing Mice (TBM)

Testing of the kinase function (ability to phosphorylate) of Lck and fyn has demonstrated a decrease in kinase function in both of these in tumor-bearing mice.

Characteristics of T Lymphocytes and Protein Expression Levels in Cancer Patients Similarly, the expression of CD3ζ protein in some human cancer patients was undetectable or markedly reduced compared to healthy i.e., not tumor-bearing, controls. The expression of CD3ζ protein was analyzed by Western blot in human cancer patients. For example, equal numbers of cells or equal amounts of proteins isolated from the lymphocytes isolated from the peripheral blood of two patients with renal cell carcinoma, one patient with liver metastases of an ocular melanoma, and a healthy individual, were analyzed using anti-CD3ζ rabbit serum. Expression of CD3ζ protein was detected in the healthy control. In contrast, the expression of CD3ζ was undetectable in the sample taken from one patient with renal carcinoma and from a patient with liver metastases of an ocular melanoma. The expression of CD3ζ protein was reduced by 95% in a second patient with renal cell carcinoma. The cancer in each of these patients was present for greater than 30 days.

Progression of cancer leads to immunosuppression of T lymphocytes. Loss in the antitumor effects of T cells in adoptive immunotherapy is correlated with a significant decrease in the cytotoxic function of CD8+ cells and changes in protein expression.

Data obtained from cancer patients including those with melanoma, renal cell carcinoma, acute lymphocytic leukemia, and multiple myeloma has shown that some patients present a marked decrease in the expression of the CD3ζ chain as determined by use of anti-ζ anti-serum 387 (obtained from Dr. Alan Weissman, NCI). In addition decreases in Fyn (UBI), Lck (UBI), and PLC-γ (UBI) have also been observed.

The observed changes in protein expression in the immunosuppressed T cells include the complete loss, or marked decrease, in the expression of the TCR subunit proteins CD3ζ and CD3γ; the appearance of Fcεγ; and the decreased expression in the signal transduction pathway proteins of these notably Lck, Fyn, PLC-γ and GAP. Functional correlates of these include loss in the ability of cells to mobilize $Ca^{2+}$ and an altered pattern of tyrosine phosphorylation.

Complete or marked decrease in the expression of CD3ζ protein was observed in three human cancer patients exhibiting presence of a tumor for >30 days. Decreased expression of TCR subunit proteins such as CD3ζ and CD3γ; expression of Fcεγ in the T lymphocytes; and decreased expression in signal transduction pathway proteins such as Lck and Fyn correlated with similar changes in T cell function including loss of cytotoxicity and loss in the ability to be stimulated. It is likely that NK cells, which also normally express CD3ζ protein, will exhibit decreased immune responsiveness with loss in CD3ζ expression.

The pattern of NF-κB/rel proteins in melanoma patients revealed alterations from the non-cancerous state. c-rel and p65 were absent in nuclear preparations. These results support use of the NF-κB/rel pattern analysis to detect cancer. Because in animal models, changes in these patterns are detected earlier that changes in the CDE zeta level of expression, analysis of these patterns may provide earlier detection of cancer in patients than the other assays of the present invention. Detection prior to clinical signs, that is as a screening assay, is contemplated.

Assays for Immunosuppression

An aspect of the present invention is to provide assays designed to determine the level of immunosuppression. These assays are useful, for example, in a patient being evaluated for adoptive immunotherapy, or organ transplantation. The assays are performed by determining changes in the expression of selected proteins known to be predictive of the level of immunosuppression of T lymphocytes. A selected protein to examine in an assay includes any one protein of the TCR subunits or the signal transduction pathway, or a combination of said proteins. Decreased expression of selected TCR subunit proteins such as CD3ζ and CD3γ; or decreased expression of selected T cell signal transduction pathway proteins such as Lck, Fyn, PLC-γ or GAP; or the increased expression of Fcεγ in T cells or T cell subsets, are diagnostic of an immunosuppressed state. These changes in protein expression in T lymphocytes or T cell subsets are associated with loss in the ability to stimulate T cells that are needed for effective adoptive immunotherapy.

Generally, the association between TCR protein expression and immunosuppression is positive, i.e., as protein expression decreases, so does the response of cells to immunotherapy. The response in humans and other animals to malignant progression is in the same direction as that observed in the murine system.

Analysis of the pattern of transcription factors of the NF-κB/rel family of proteins provide an assay for immunosuppression. The pattern includes whether at least one protein is present or absent. The pattern is a vector of 0 or 1, for presence or absence respectively, as determined by Western blots, or similar methods. Antibodies directed to the components of the system are useful to determine if the proteins are present. In some abnormal states, a protein present in the normal state has been replaced by one or more proteins of different molecular weights. In these situations, an antibody directed to the part of the protein that is not present in the replacement proteins, may be used to ascertain whether the substitution has occurred, in which case a complex will not form.

Methods for Determining Protein Expression Levels

The expression levels of TCR subunit proteins, of Fcεγ, or of selected proteins in the T cell signal transduction pathway, are suitable for use in an immunosuppression assay. One or a combination of proteins, is used. Many different conventional and well known assay methods are suitable to evaluate the level of expression of selected proteins in T lymphocytes. Samples of tissue or fluid such as blood are isolated from the patient and the level of expression of the selected TCR subunit protein, Fcεγ, or selected protein in the T lymphocyte signal transduction pathway is determined. These samples are taken from various tissues including tumor tissue, splenic or lymphatic tissue, peripheral blood cells, cerebrospinal fluid, pleural effusions, and ascites.

A protein extract of the tissue or cell sample is analyzed directly to determine the level of expression of protein. Alternatively, T cells, or T cell subsets, are purified before determining the level of expression of the selected protein. T cells and T cell subsets are purified by any of a variety of conventional techniques such as rosetting followed by Ficoll-Hypaque gradient centrifugation, indirect panning, antibody/complement-mediated cytotoxicity, immunomagnetic purification, flow cytometry, and similar techniques. Additionally, the TCR are immunoprecipitated using an antibody such as anti-CD3ε. The subunit proteins comprising the TCR are analyzed by Western blot by methods known to those of skill in the art.

The level of expression of a protein is determined using well known techniques such as immunofluorescence, ELISA, Western blot analysis, and similar techniques. An extract for analysis of protein by any of these well known techniques is made by conventional methods from the tissue or fluid sample, or T cells or T cell subsets prepared from these samples. An antibody which specifically detects the selected protein, and which is conjugated to a known label, is prepared by methods known to those of skill in the art.

Clinical Evaluation for Organ Transplantation
Using Protein Expression Assays

It is contemplated that the methods of the present invention are useful in monitoring and facilitating transplantation of organs and tissues. A patient is currently prepared for a transplant by means of various treatments designed to increase the level of tolerance. These treatments include repeated transfusions with white blood cells or total blood.

Immunosuppression is induced by administering to a patient, the soluble immunosuppressive factor of the present invention in a pharmaceutically acceptable carrier. Effective amounts are determined empirically.

It is possible to monitor the level of expression of selected TCR subunit proteins, Fc$\epsilon\gamma$, and proteins in the T lymphocyte signal transduction pathway during preparation of the patient in order to determine the level of immunosuppression in the patient and thereby ascertain when patients are sufficiently immunosuppressed to receive the transplant.

The methods of the present invention are used to determine the level of immunosuppression in the patient and thereby provide information needed to properly time treatment to maintain tolerance. Agents isolated using the screening methods of the present invention, capable of increasing immunosuppression in the patient, are expected to have utility for the successful preparation and maintenance of the transplant patient.

Selection of Patients for Immunotherapy

In determining a therapeutic strategy, a physician assays the expression of TCR-related proteins of a patient's own T lymphocytes in order to evaluate the patient's level of immunosuppression, thereby predicting the likelihood of success that these cells can be stimulated for effective immunotherapy. This is useful for any therapy employing the patient's own cells, e.g. cytokine therapy or autologous adoptive therapy. It is further contemplated that T cells evaluated according to the present invention are selected for allogeneic and syngeneic treatment protocols in cases where a patient's own T cells are immunosuppressed. Even in instances in which adoptive immunotherapy is not contemplated, it is expected that evaluation of the level of immunosuppression will aid the physician in determining when to treat with antibacterial agents, immunostimulating drugs, and the like. Another use is to monitor immunosuppression in autoimmunity before transplantation to determine the optimal level of suppressive drug being administered as well as the timing of the transplant.

Patients are selected for immunotherapy, for example, for autologous adoptive immunotherapy based on level of expression, or the pattern, of a selected protein or proteins. Selection criteria are that expression levels and/or patterns are not below the threshold for response to lymphocyte stimulation. The threshold level for response to lymphocyte stimulation is empirically derived for each combination of disease and selected protein and is relative to individuals believed to have normal immunological responses. For example, with one combination of a selected protein and a particular disease, it may be found that the selected protein must be produced at levels substantially equivalent to that found in healthy individuals in order for autologous adoptive immunotherapy to be effective. With yet another combination of a selected protein and a disease, autologous adoptive immunotherapy may still be effective with only a relatively low level of expression of the selected protein.

Alternatively, the expression of the gene encoding the selected protein in T cells or T cell subsets is ascertained by any of a variety of methods including Northern hybridization or in situ hybridization. If the gene is known to only be expressed in the T lymphocytes, RNA is isolated from the tissue or cell samples. Alternatively, RNA may be obtained from purified T cells or T cell subsets prepared from these samples, using conventional methods. The RNA is hybridized with labeled DNA or a hybridization probe which specifically detects the mRNA encoding the selected protein.

Alternatively, patients are selected for adoptive immunotherapy on the basis of their protein expression ratio. The expression ratio (E.R.) is the number of T cells which express a selected TCR subunit protein, or protein in the T lymphocyte signal transduction pathway, divided by the total number of T cells counted. For example, the expression ratio can be determined by means of two-color or three-color flow cytometry according to methods such as those described in *Current Protocols in Immunology*, Vol. I, J. E. Coligan, A. M. Kruisbeek, D. H. Margulies, E. M. Shevach and W. Strober (eds.), Green Publishing Associates and Wiley-Interscience, 5.1.1-5.4.15 (1991), incorporated herein by reference.

For components of the TCR that are on the interior of the membrane or components of the signal transduction pathway, the cell is made permeable to the label. For example, lymphocytes isolated from the patient are exposed to two different antibodies each of which is conjugated to a different dye. One antibody is used to detect cells expressing the selected TCR subunit protein, or protein in the T lymphocyte signal transduction pathway, and this antibody is conjugated to a dye such as fluorescein isothiocyanate (FITC). A second antibody binds to a protein found in all T cells, such as CD3, and this antibody is conjugated to a second dye such as phycoerythrin. The fraction of T cells expressing the selected TCR subunit protein or T lymphocyte signal transduction pathway protein is determined by analysis of the samples using flow cytometry.

As described in preceding sections, patients are selected for autologous adoptive immunotherapy based on level and/or pattern of protein expression. Selection criteria are that expression is not below the threshold level for response to lymphocyte stimulation, wherein the threshold level for response to lymphocyte stimulation is empirically derived for each combination of disease and selected protein.

For example, with one combination of selected protein and disease, it may be found that at least 50% of the T cells must express the selected protein (E.R.=0.5) if autologous adoptive immunotherapy is to be effective. With yet another combination of selected protein and disease, expression of the protein in at least 70% of the T cells (E.R.=0.7) may be required if autologous adoptive immunotherapy is to be effective. In another combination of selected protein and disease, presence of p65 may be required.

Monitoring Efficacy of Chemotherapy,
Radiotherapy and Surgery for Cancer

If chemotherapy, radiotherapy or surgery is effective in eliminating the majority of a tumor, then the immunosuppressed proteins should return to normal levels and patterns. These improvements are monitored by the methods of the present invention.

It is contemplated that conventional treatments and protocols are used to complement and supplement the methods of the present invention. As the tumor size or load of the patient is decreased using non-biological treatments, e.g. chemotherapy, the level of immunosuppression will also abate. Additionally, agents which reverse immunosuppression are identified by the methods of the present invention. These treatments or agents can be followed or supplemented with autologous adoptive immunotherapy. Effective timing of autologous adoptive immunotherapy is predicted by measuring the level of immunosuppression in the patient by methods of the present invention, for example, by determining the level of expression of selected TCR subunit proteins; Fcεγ in T lymphocytes; proteins in the T lymphocyte signal transduction pathway; and proteins in the NF-κB/rel family.

The methods that are suitable to supplement or complement autologous adoptive immunotherapy include surgery; radiation or treatment with chemotherapeutic or pharmacological agents. The chemotherapeutic or pharmacological agents include all cytokines; agents which reduce tumor size or load including cyclophosphamide, adriamycin, steroids, flavonoids and IL-2; growth hormones; cimetidine; chloroquine; non-steroidal anti-inflammatories such as aspirin, ibuprofen, indomethacin, and levamisole.

Several different strategies are available to circumvent immunosuppression of T lymphocytes. Immunotherapeutic activity of T lymphocytes are restored by recombinant methods. The level of expression of selected TCR subunit proteins, T lymphocyte signal transduction pathway proteins, or NF-κB/rel are restored in immunosuppressed cells by introducing into said cells an expression vector comprising the gene encoding a selected protein. The expression of a gene in the recombinantly engineered cells restores normal levels of the protein to the lymphocytes. These recombinantly engineered lymphocytes are stimulated for adoptive immunotherapy using any of the alternative methods herein described.

Liposome Delivery System

Although free cytokines such as IL-2 are suitable for the method of the present invention, a cytokine is preferably incorporated into liposomes as a delivery system. Liposomes are phospholipid vesicles which are capable of containing a designated amount of a cytokine or other bioactive compounds, depending on the type of interaction between a solute and a phospholipid used to prepare a liposome. Methods for the preparation of liposome-encapsulated cytokines are disclosed in co-pending application Ser. No. 07/382,778, the disclosure of which is incorporated in its entirety herein by reference.

Several routes of administration are suitable for the administration of liposomes, for example, intravenous, subcutaneous, intraperitoneal, and oral delivery. Important advantages of liposomal delivery include the tissue distribution and binding properties as compared to the free forms of the bioactive ingredient, resulting in enhanced therapeutic index and decreased toxicity.

Treatment of Mice with IL-2 Liposomes

Two experiments have been done treating mice (bearing tumor for 14 days) with intraperitoneal IL2-liposomes (50,000 U/mouse/day×5 days). The mice were then sacrificed on day 32 after tumor injection, and the splenic lymphocytes were assayed for the expression of ζ. Mice receiving IL2-liposomes demonstrated normal levels of the ζ chain whereas non-treated animals had completely lost the expression of this chain. It is possible therefore that IL2-liposomes protect from the loss of ζ induced by tumor. However, an alternative possibility is that the liposomes non-specifically expand T cells such that the loss of ζ could be masked by the expanded populations.

Clinical Use of Stimulated T Cells

In an illustrative embodiment, stimulated T cells are collected and placed in the body of an organism, preferably a mammal, such as a mouse or a human, where they facilitate immunotherapeutic activity, e.g. cytotoxic activity, or lymphokine production, upon administration of IL-2. More preferably the cells are placed in the body of a human for immunotherapeutic treatment. The cells are administered to a patient using any of the conventional and well known methods and routes, e.g. those described in S. A. Rosenberg, U.S. Pat. No. 4,690,915, incorporated herein by reference. These routes include intravenous, intraarterial or intracavitary administration, encompassing intrapleural, intraperitoneal, intrathecal, intravesical, and the like.

Generally, after the administration of an effective amount of IL-2 in vivo, the cells display an enhanced proliferation and antitumor activity. The administration of IL-2 preferably occurs over a period of about 7 days. The amount of IL-2 effective for enhancing cell proliferation and immunotherapeutic activity in vivo depends on the mammal being treated. For example, about 0,000–70,000 units/day of IL-2, preferably about 50,000 units/day of IL-2, are administered to mice, and about $1\times10^6$ to $6\times10^6$ International Units/m²/day are administered to humans.

As mentioned in the previous section, it is preferred that the T cells are initially stimulated for less than 24 hours with anti-CD3 MAb, with or without any IL-2 present. It is within the scope of the invention to include IL-2 with the anti-CD3 MAb in the initial culture, if desired. Although this is suitable and produces similar results, it is not necessarily preferred, at least because of the undesirable expense of IL-2. Rather, it is preferable to stimulate cells with anti-CD3 Mab alone, collect the stimulated cells, infuse the stimulated cells into an immunosuppressed mammal, and then administer IL-2 to the mammal.

Interleukin-2 is a commercially available T cell growth factor. Both naturally occurring IL-2, such as might be derived from cultured rat splenocytes or from the Jurkat cell line, or recombinant IL-2 (rIL-2) are suitable. It is believed that other cytokines can also be used in the present invention to produce the cytokine-activated cells. A naturally occurring cytokine, or recombinantly produced cytokine is used. These include IL-1, IL-4, IL-6, IL-12, TNF, GM-CSF, interferon, and the like. It is envisioned a cytokine may be used alone or in combination with other cytokines, including IL-2, either added to the culturing medium or administered to a patient. Combinations of rIL-2, flavonoids and chemotherapeutic agents are also effective in reducing tumors, at least in animal models (Wiltrout et al., 1991). T Cells are essential for this anti-tumor response. Commercial sources of recombinant human and murine cytokines are available. *Current Protocols in Immunology,* Vol. I, J. E. Coligan, A. M. Kruisbeek, D. H. Margulies, E. M. Shevach and W. Strober (eds.), Green Publishing Associates and Wiley-Interscience, 2.4.1-2.10.3 (1991).

Use of Immunorestorative Agents

It is contemplated that the immunorestorative agents identified using the methods of the claimed invention will have utility in the treatment of diseases characterized by progressive immunosuppression by reversing immunosuppression. These agents are identified by providing a mammalian T lymphocyte preparation wherein the level of expression of at least one selected TCR subunit protein or protein in the signal transduction pathway, or pattern of the NF-κB/rel proteins, is subnormal compared to healthy, non-immunosuppressed individuals of the same mammalian species; the lymphocyte preparation is cultured in the presence of an agent to be tested, generally an agent suspected of reversing immunosuppression; and the level of expression and/or pattern of the selected protein is determined. Alternatively, the agent is administered to a subject with subnormal expression of a TCR subunit protein or protein in the T lymphocyte signal transduction pathway and the level of expression of said protein is determined in a sample obtained from the patient after treatment.

Agents capable of significantly increasing the level of expression of selected TCR subunit proteins or proteins in the T lymphocyte signal transduction pathway, and/or of restoring the presence of proteins of the NF-κB/rel system, present a method of reversing immunosuppression in a diseased animal or human. The agent is administered to the subject, optionally with or without T cell surface receptor antibodies and/or cytokines for the stimulation of lymphocytes, in order to reverse immunosuppression in the diseased subject. Alternatively, lymphocytes isolated from the subject are treated in vitro with the agent and administered to the patient for adoptive immunotherapy. For example, the lymphocytes could be cultured in the presence of flavonoids. These lymphocytes are optionally stimulated in vitro or in vivo, with or without T cell surface receptor antibodies and/or cytokines.

Subgroups of patients may be identified and evaluated which may not show a response to one combination of agents, but may to others. Non-responders to anti-CD3, for example, may respond if flavonoids and IL are added. The additional agents may "rescue" patients previously intractable to therapy.

Restoration of Immunological Function Using Recombinant Techniques

Methods known to those of skill in the art are used for the construction of an expression vector carrying the selected gene of interest as well as for the introduction of said vector into immunosuppressed T cells. To restore immunological function, a gene encoding an immunorestorative agent is included in the vector. This gene could be an antisense gene to the immunosuppressive factor of the present invention. The gene is operably linked to a promoter, which is generally a regulatable promoter. The vector is introduced into T lymphocytes using well known transfection protocols such as calcium phosphate transfection or transfection by electroporation. The selected gene is introduced and expressed in T cells using well known vectors, e.g. retroviral vectors. *Current Protocols in Molecular Biology*, F. M. Ausubel et al. (eds.), Greene Publishing Associates and Wiley-Interscience, 9.0.1-9.14.3 (1989).

Reexpression of the CD3ζ Chain

Culturing of lymphocytes from tumor-bearing mice for 48 hours in tissue culture media (RPMI 1640+additives, but no fetal bovine serum) containing any of the following combinations induces a re-expression of the CD3ζ chain:

A. Ionomycin (1 μg/ml) (Calbiochem, La Jolla, Calif.)

B. Ionomycin+Phorbol Miristic Acetate (10 ng/ml) (Chemsyn Science Labs., Lenexa, Kans.).

C. Ionomycin+IL2 (300 U/ml).

D. Ionomycin+PMA+IL2

E. Ionomycin+anti-CD3+IL2

F. Anti-CD3 monoclonal antibody (10 ng/ml)

G. Flavonoids+IL-2

H. Anti-CD3+flavonoids

Use of Immunosuppressive Agents

Immunosuppressive agents identified using the methods of the claimed invention are likely to have utility in the treatment of autoimmune diseases. Of particular interest in this regard are soluble factors produced by a tumor which cause T cell immunosuppression. These agents are identified by providing a mammalian T lymphocyte preparation wherein the level of expression of at least one selected TCR subunit protein, or protein in the signal transduction pathway is normal compared to healthy individuals of the same mammalian species. Another assay is whether alterations are present in the pattern of NF-κB/rel proteins. The lymphocyte preparation is cultured in the presence of an agent suspected of causing immunosuppression, and the level of expression and/or pattern of said protein is determined. Alternatively, the agent is administered to a healthy subject and the level of expression of at least one selected TCR subunit protein or protein in the lymphocyte signal transduction pathway is determined. The agents are isolated and further purified by fractionating the immunosuppressive supernatant to locate the active fraction, and applying methods of qualitative analysis to identify the nature of the factor.

Agents capable of decreasing the level of expression of selected TCR subunit proteins or proteins in the T lymphocyte signal transduction pathway, and/or the pattern of NF-κB/rel proteins, present a method of inducing immunosuppression in an animal or human. The agents or the soluble immunosuppressive factor of the present invention are administered to the subject. Alternatively, a nucleotide sequence encoding at least the immunosuppressive sites of the soluble factor, is transfected into cells, generally cells of the recipient, and administered to the mammal.

The following examples are set forth as representative of specific and preferred embodiments of the present invention. These examples are not to be construed as limiting the scope of the invention in any manner. It should be understood that many variations and modifications can be made while remaining within the spirit and scope of the invention.

EXAMPLE 1

Loss of Antitumor Effects of T Cells Isolated From Long-Term Tumor-Bearing Mice

T cells isolated from long-term TBM have no detectable antitumor effects when used in adoptive immunotherapy ("Long-term" is used interchangeable with "late" herein). The generation of T-activated killer (TAK) cells was accomplished as described in C. M. Loeffler et al., *Cancer Res.*, 51:2127 (1991), which is incorporated herein by reference. C57BL/6 murine splenocytes were placed on a Ficoll-Paque gradient (Pharmacia) for isolation of lymphocytes. After washing with HBSS (GIBCO, Grand Island, N.Y.) two times, red blood cells (RBC) were lysed with distilled water and the remaining mononuclear cells counted. The cells were then placed over a mouse T cell rapid affinity chromatography column (Biotex Laboratories Inc., Edmonton Canada) for T cell enrichment. Cells were washed with HBSS two times, activated with anti-CD3 MAb (145-2Cll) and IL-2 (specific activity, $1.5\times10^7$ U/mg; Hoffmann-LaRoche Inc., Nutley, N.J.). T-enriched cells were incubated in culture flasks at a concentration of $1.5\times10^6$ cells/ml of TCM consisting of Rosewell Park Memorial Institute (RPM1) 1640 (available from GIBCO, Grand Island, N.Y.) supplemented with 25 mM HEPES [N-2-hydroxyethyl)piperazine-N'-(2-ethanesulfonic acid)], 2 mM L-glutamine, 5% fetal calf serum, 100 U/ml penicillin, 100 μg/ml streptomycin, 10 mM non-essential amino acids, 100 mM sodium pyruvate, and 25 μM 2-mercaptoethanol. To generate T-AK cells, 2 μg of 145-2Cll MAb was added per ml of TCM. Cells were incubated overnight at 37° C. in 5% $CO_2$ after which they were harvested, washed twice in HBSS, resuspended in HBSS containing 30 U/ml of IL-2, counted and injected into mice.

Methods for demonstrating the therapeutic efficacy of T-AK cells used in conjunction with liposome-encapsulated IL-2 (IL-2 liposomes), were done as described in C. M. Loeffler et al., *Cancer Res.*, 51:2127 (1991), which is incorporated herein by reference. Approximately $3.0\times10^5$ MCA-38 cells in 0.5 ml of HBSS were injected intrasplenically in 6- to 8-week old C57BL/6 mice using a 30-gauge needle. Each experimental group consisted of at least 10 C57BL/6 mice. After three days, mice received a single intravenous injection of $4.0\times10^7$ T-AK cells from either normal mice, early TBM (subcutaneous tumor present for 14–21 days) or late TBM (subcutaneous tumor present for greater than 30 days). In addition, mice received once-daily intraperitoneal injections of IL-2 liposomes (50,00 U per day) on days 3–7 following tumor inoculation. The number of hepatic metastases was evaluated in each therapeutic group on day 12 after tumor inoculation. One to 2 ml of a 15% India ink solution was injected into the superior mesenteric vein of anesthetized mice. The liver was removed and placed in Fekete's solution (30 ml formalin and 15 ml glacial acetic acid in 300 ml of 70% ethanol). Hepatic metastases were counted and a Student's unpaired T-test was used to evaluate the significance of differences between treatment groups.

The data presented in FIG. 1 illustrates representative results obtained in three separate experiments. Untreated mice had 236±30 liver metastases by day 11. Mice treated with T-AK cells from a non-tumor-bearing mouse (normal) had 99±23 metastases while T-AK cells from early TBM produced an even greater reduction in the number of metastases to 48±16. T-AK cells obtained from late TBM failed to produce any therapeutic effect because hepatic metastases numbered 229±41. The therapeutic efficacy of T-AK cells is therefore dramatically reduced when these cells are obtained from late TBM.

EXAMPLE 2

Significant Decrease in In Vitro Cytotoxicity in T Lymphocytes from Long-Term TBM The in vitro cytotoxicity of lymphocytes from long-term TBM is significantly decreased from the non-malignant state. Standard chromium release assays were performed using as effectors, T-AK cells which were maintained in culture with 100 U of rIL-2 after the initial stimulation with anti-CD3. Assays were performed on days 2, 4, and 7 of culture. Tumor targets ($4\times10^6$ml) ) were incubated with 150 μCi $Na_{51}CrO_4$ (1000 μCi/ml; New England Nuclear Products, Boston, Mass.) at 37° C. for 60 min. The targets were washed twice with TCM, resuspended in media, and counted. T-AK effector cells were washed twice and then aliquoted in triplicate in U-bottom microtiter plates (Costar) and serially diluted 2-fold to yield effector:target cell ratios ranging from 24:1 to 3:1. Five thousand targets were added per well. Spontaneous release wells contained target cells in culture media only. The maximum release well contained target cells in detergent. Plates were incubated for 4 h at 37° C. in 5% $CO_2$. The supernatant was harvested and radioactivity was counted in a gamma counter (LKB 1272). The percentage of specific cytotoxicity was determined by the formula:

$$\frac{\text{Experimental mean cpm-spontaneous mean cpm}}{\text{Maximal mean cpm-spontaneous mean cpm}}\times100 = \% \text{ of cytotoxicity}$$

Figure 3:
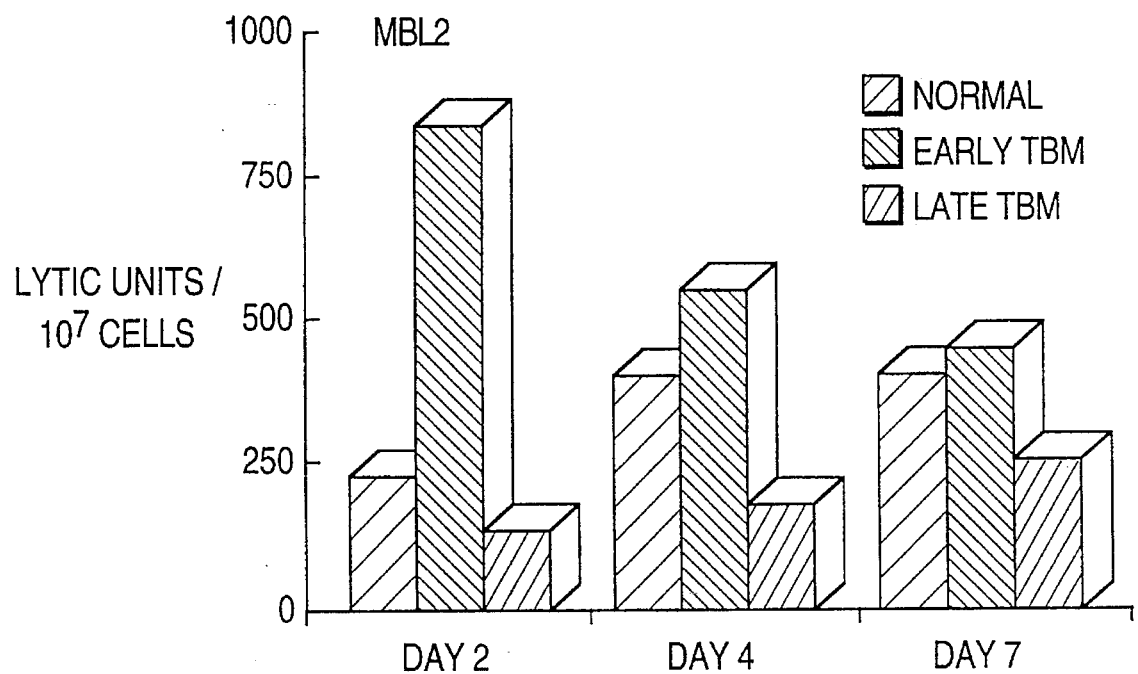
FIG. 3 illustrates the cytolytic activity of normal, early and late TBM T-AK cells against MBL2. Enriched T cells were activated with anti-CD3 and cultured in TCM containing 100 U rIL-2/ml. Lytic activity was tested on days 2, 4 and 7 of culture in a 4-hr chromium release assay.
Figure 2A:
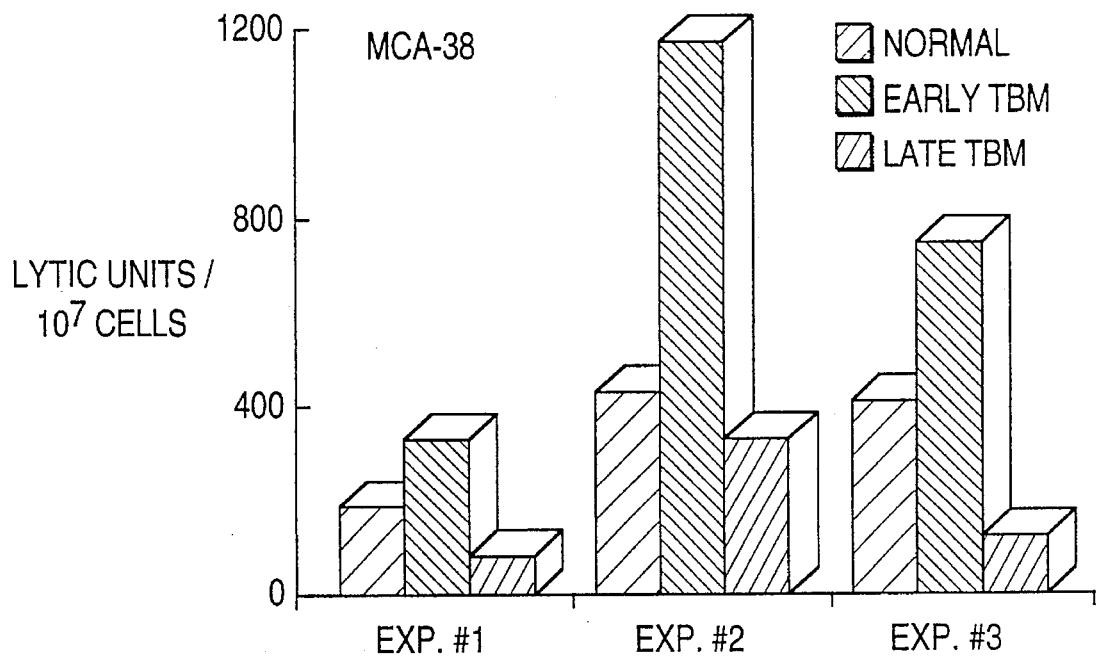
FIG. 2 illustrates (A) the cytolytic activity of normal, early and late TBM T-AK cells against MCA-38 (colon carcinoma); (B) the cytolytic activity of normal, early and late TBM T-AK cells against MBL2 (lymphoma); and (C) the cytolytic activity of normal, early and late TBM, T-AK cells against RENCA (renal cell carcinoma) tumor cell lines. Enriched T cells were activated with anti-CD3 and cultured in tissue culture medium (TCM) containing 100 U recombinant interleukin-2/ml (rIL-2/ml). Lytic function was tested on day 2 of culture.
Figure 2B:
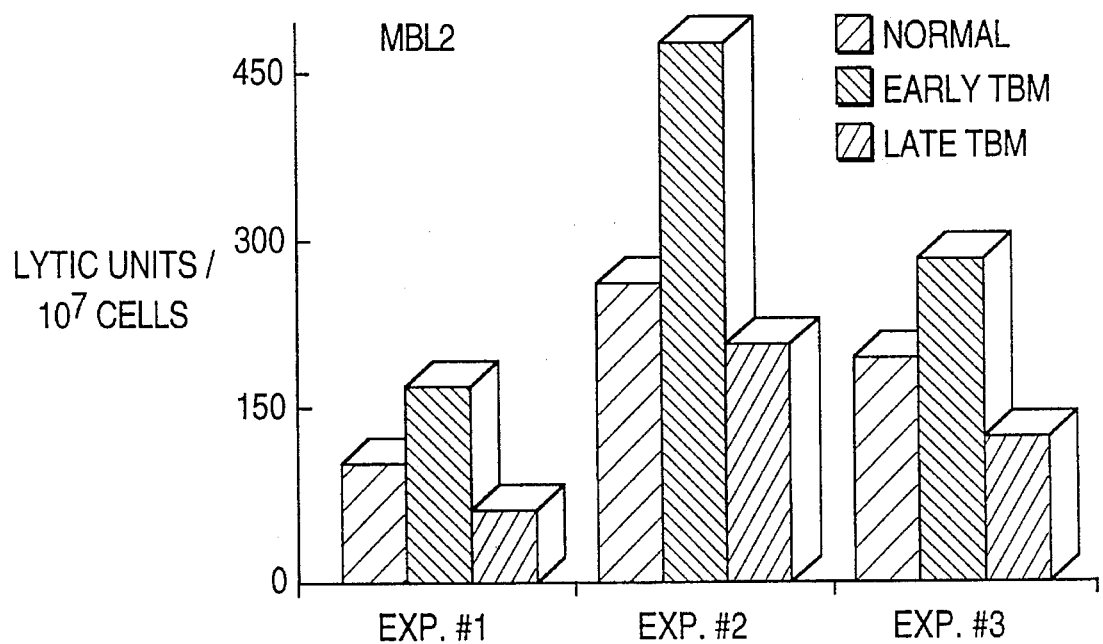

At day 2 of culture, cytolytic activity was consistently highest in the early TBM cells (FIG. 2) while that of both non-tumor-bearing (normal) or late TBM cells was lower. Lytic function of cells from normal mice on day four of culture had increased significantly, but it was still highest in early TBM (FIG. 3). Late TBM lymphocytes had the lowest lytic function.

Only after 7 days in culture did lymphocytes from late TBM show any significant increase in lytic function (FIG. 3). Lytic activity was also observed against the syngeneic target MBL2 (lymphoma) and an allogeneic target, RENCA (renal cell carcinoma). The absolute levels of cytotoxicity varied with the targets, but early TBM cells were consistently the most lytic, and the late TBM cells always had the lowest activity.

Cytotoxicity assays were performed using $CD8^+$-enriched preparations from early and late TBM. Enriched T cell preparations were made by passing a single cell splenocyte suspension through a T cell column (Biotex Laboratory Inc., Edmonton, Canada) following the kit instructions. To enrich for $CD8^+$ cells, T-enriched cells were incubated with 1 μg/$1.0\times10^6$ cells of anti-L3T4 (500 μg/ml; Becton Dickinson, Mountain View, Calif.) for 30 min at 4° C. The cells were washed twice in HBSS. Goat anti-mouse IgG Fc-specific coated magnetic beads (Advanced Magnetics Inc., Cambridge, Mass.) were washed with PBS twice and incubated with PBS and mixed with the T-enriched cells at a bead:cell ratio of 25:1 at 4° C. for 30 min and then separated on a magnetic separator (Advanced Magnetics). The last step was repeated twice. Unbound cells were removed and washed twice with HBSS. $CD8^+$-enriched cells had less than 2% $CD4^+$ contaminating cells. Phenotypic analysis of the enriched cell preparations showed greater than 95% $CD8^+$.

$CD8^+$-enriched cells showed lytic activity similar to that of unseparated lymphocytes (Table 1). To eliminate the potential confounding effects of even small numbers of contaminating cells, $CD8^+$ cells were also positively sorted by FACS, cultured with anti-CD3+IL-2 and tested for lytic function. Positive cell selection by FACS was performed with T-enriched cells from fresh splenocyte preparations (greater than 95% Thy $1.2^+$ cells). These cells were incubated with 1 μg/$1.0\times10^6$ cells of anti-Lyt.2 FIT and anti-L3T4 (500 μg/ml; Becton Dickinson) for 30 min at 4° C. The cells were then sorted into $FITC^+$ ($CD8^+$ cells) and $PE^+$ ($CD4^+$ cells) on a FACStar Plus flow cytometer (Becton Dickinson).

The lytic activity of the early TBM $CD8^+$ lymphocytes was again the highest while that of late TBM cells was the lowest (Table I). In all experiments, the results remained similar regardless of whether the effector cells were enriched T cells, enriched CD8$^+$ or pure CD8$^+$ cells. The increase in cytotoxicity seen in late TBM CD8$^+$ cells after seven days in culture may be due to an increase in the lytic function of the originally suppressed CD8$^+$ cells or due to the expansion of a small subset of CD8$^+$ cells which were never suppressed.

TABLE I

Cytotoxic activity of T cells from normal mice, early TBM, and late TBM[a]

| | Lytic U/10$^7$ cells |
|---|---|
| T enriched cells | |
| Normals | 259 |
| Early TBM | 319 |
| Late TBM | 189 |
| CD8$^+$ cells (CD4$^+$ depleted) | |
| Normals | 254 |
| Early TBM | 469 |
| Late TBM | 162 |
| CD8$^+$ cells (positive sort) | |
| Normals | 278 |
| Early TBM | 1161 |
| Late TBM | 125 |

[a]Cytolytic activity of T-enriched, CD8$^+$ cells obtained by CD4$^+$ depletion or cell storing. Cells were activated with anti-CD3 and cultured in TCM with 100 U IL-2/ml for 3 days.

EXAMPLE 3

Phenotypic Analysis of T-Enriched Cell Preparations from Fresh Splenocytes of Normal Mice, Early TBM and Late TBM The abnormal activity of late TBM cells is not related to large alterations in T cell subsets or distributions. To determine if a difference in the percentage of T-lymphocyte subsets could explain the difference in lytic function, phenotyping was done in the following manner. Fresh splenocytes from the various groups of mice were enriched for T cells and purified to remove contaminating tumor cells. The data was obtained from cell preparations that were greater than or equal to 95% Thy 1.2$^+$.

There was a consistent, but not significant decrease in the L3T4$^+$ populations from late TBM (Table II). The CD4/CD8 ratios in these mice, however, remained within normal limits. The phenotypes of fresh splenocytes not enriched for T cells, obtained from the same groups of mice, did not show any significant change in the cell subsets. Large alterations in T cell subsets or distribution, therefore, is not related to the abnormal activity of late TBM.

TABLE II

Phenotypic analysis of T-enriched cells from normal mice, early TBM, and late TBM[a]

| | Thy 1.2 | CD 3 | Lyt.2 | L3T4 | Mac 1 |
|---|---|---|---|---|---|
| Normals | 98% | 86% | 37% | 54% | 2% |
| Early TBM | 97% | 89% | 30% | 58% | 3% |
| Late TBM | 95% | 86% | 34% | 48% | 3% |

[a]Phenotypic analysis of T-enriched cells from normal and tumor-bearing mice (TBM). Flow cytometry was performed on T lymphocytes isolated from spleens of mice bearing tumor for different lengths of time. T lymphocytes were enriched on a T cell column (Cellect, Biotex) immediately after isolation.

EXAMPLE 4

No Major Differences Were Observed in the Levels of Lymphokines in Supernatants of Activated T-Enriched Cells from Normal Mice, Early TBM and Late TBM In order to determine if inadequate function of the CD4$^+$ helper cell subset was the principal cause of the decreased immunological responsiveness in late TBM, lymphokine levels in the supernatants of activated T-enriched cells from normal mice, early TBM and late TBM were compared. Samples of supernatants were collected at 24, 48 and 72 h. IL-1$\alpha$ was measured using mouse Interest I-$\alpha$ Elisa (Genzyme, Cambridge, Mass.). Biologically active protein was confirmed using the IL-1 mouse thymocyte bioassay. IL-2 levels were tested with the IL-2 Elisa Kit (Collaborative Research, Inc., Bedford, Mass.) and confirmed with the IL-2 bioassay using the IL-2-dependent cell line, CTLL-2 (ATCC). IL-6 levels were measured with the murine IL-6 Elisa Kit (Endogen Inc., Boston, Mass.) and confirmed with the murine bioassay utilizing the plasmacytoma cell line Tl165 (Genetics Institute). Total murine interferons were measured with the L929 (ATCC) virus bioassay. TNF-$\alpha$ levels were measured with the 1929 mouse fibroblast cell line (ATCC).

There were no major differences in the levels of lymphokines measured in the early and late TBM T-AK cultures in three different experiments. The data after 48 h in culture, from two of these experiments, is shown in Table III. Significant differences in lytic function were observed in these same experiments. Lymphokine production was therefore quantitatively and qualitatively similar in the supernatants of activated T-enriched cells from normal mice, early and late TBM.

TABLE III

Lymphokine levels in supernatants of activated T-enriched cells from normal mice, early TBM and late TBM[a]

| | IL-1[b] | IL-2[c] | IL-6[b] | IFN[c] |
|---|---|---|---|---|
| Experiment #1 | | | | |
| Normal | 24 | 3.0 | 850 | 20 |
| Early TBM | 48 | 6.5 | 1000 | 60 |
| Late TBM | 40 | 6.0 | 1250 | 40 |
| Experiment #2 | | | | |
| Normal | 0 | 4.5 | 1200 | 16 |
| Early TBM | 90 | 7.5 | 1250 | 130 |
| Late TBM | 75 | 9.0 | 1250 | 180 |

[a]Lymphokine levels in supernatants of T-enriched cells from normal and TBM activated with anti-CD3. Samples were obtained at 24, 48, and 72 h. Data presented are from 48 h.
[b]pg/ml
[c]I.U./ml

EXAMPLE 5

CD4$^+$ Cells from Late TBM Have Adequate Helper Function

CD4$^+$ lymphocytes in late TBM are more active as helper cells than CD4$^+$ cells from normal animals. Mixing experiments were done to test whether CD4$^+$ cells from late TBM would enhance or suppress the development of lytic function in normal CD8$^+$ cells. Purified CD4$^+$ and CD8$^+$ lymphocytes were cocultured in 24 mm wells separated by a membrane with 4 μm size pores. This pore size allows for free exchange of soluble components. Cytotoxicity assays were performed on day 2 of culture.

CD8+ cells from normal mice showed an increased lytic activity (655 L.U.) when cocultured with CD4+ cells from late TBM compared to their lytic activity (204 L.U.) in the presence of normal CD4+ cells (Table IV). CD4+ cells from late TBM were able to support the high lytic function of early TBM CD8+ lymphocytes (1075 L.U.) even better than normal CD4+ cells (482 L.U.). CD4+ lymphocytes are not responsible for suppressing the function of CD8+ cells in late TBM because these cells are more active as helper cells than CD4+ cells from normal animals.

TABLE IV

CD4+ cells from late TBM do not suppress lytic function in CD8+ cells[a]

| Source of Cells | | | |
|---|---|---|---|
| Late TBM | Early TBM | Normal | Lytic U/10$^7$ cells |
| CD4+/CD8+ | — | — | 139 |
| — | CD4+/CD8+ | — | 1375 |
| — | — | CD4+/CD8+ | 204 |
| — | CD4+ | CD8+ | 1058 |
| CD8+ | CD4+ | — | 354 |
| CD4+ | — | CD8+ | 655 |
| CD4+ | CD8+ | — | 1075 |
| CD8+ | — | CD4+ | 104 |
| — | CD8+ | CD4+ | 482 |

[a]Mixing experiments were performed by combining freshly isolated cell subsets in 24 mm wells after stimulation with anti-CD3 and IL-2. Experiments were also performed utilizing Costar "Transwell" plates where the subsets are separated by a membrane containing 0.4 μm pore size. Lytic function was tested against MBL2 lymphoma three days after starting the culture.

EXAMPLE 6

CD8+ Cells from the Late TBM Do Not Suppress Other CD8+ Cells

CD8+ cells from late TBM are defective. CD8+ cells from late TBM are poor in lytic activity when cocultured with CD4+ cells from any source. When cocultured with the most highly active CD4+ cells from early TBM, CD8+ cells from late TBM had ⅓ to ¼ the total lytic activity of CD8+ cells from normal mice or early TBM. Coculture experiments performed in regular 24 mm wells which permit cell-cell contact between CD4+ and CD8+ cells showed very similar results where once again, CD8+ cells from late TBM had ⅓ to ¼ the total lytic activity of CD8+ cells from normal mice or early TBM. Mixing experiments using CD8+ cells from early and late TBM gave no indication that CD8+ cytolytic activity is suppressed by other CD8+ suppressor cells. Even in the presence of adequate helper function CD8+ cells from late TBM were weakly cytotoxic suggesting that CD8+ cells are the target of tumor-mediated immune suppression.

EXAMPLE 7

Inhibition of Cytoxic Activity of Normal Cells by Supernatants from MCA-38 Cell Cultures The absence of suppressor activity within the lymphocyte subsets from late TBM suggested that the inhibiting signal(s) might originate from the tumor itself. Titration experiments were performed using increasing concentrations of supernatants from MCA-38 cell cultures making sure the concentration of IL-2 was kept constant. Lymphocytes were activated with anti-CD3 and cultured with 100 U/ml of IL-2. Cultures were started at 1.5×10$^6$ cells/ml and cell counts and cytotoxicity assays were performed on day 3 of culture.

The cytolytic activity of lymphocytes cultured in media containing as little as 30% supernatant from MCA-38 cells was decreased by 30–45% (Table V). TGF-β is a tumor-associated cytokine that has been implicated in tumor-mediated immune suppression. Antibodies to TGF-β, however, did not diminish the inhibitory effects of the tumor supernatant. Two bioassays failed to detect any TGF-β activity in the tumor supernatant.

Similar inhibitory effects were mediated by supernatants of the MBL-2 lymphoma. The inhibitory effects of the tumor is therefore not limited to the MCA-38 model system. These data suggest that a soluble tumor product(s) inhibits the development of cytotoxic function in CD8+ cells in late TBM.

TABLE V

Suppression of in vitro cytolytic activity of normal lymphocytes by tumor cell supernatant[a]

| | Lytic U/10$^7$ Cells | | |
|---|---|---|---|
| | Exp. 1 | Exp. 2 | Exp. 3 |
| Normals | 138 | 93 | 118 |
| 10% supernatant | 126 | 116 | 126 |
| 30% supernatant | 99 | 89 | 66 |
| 50% supernatant | 83 | 48 | 21 |

[a]Suppression of cytolytic activity of normal lymphocytes by supernatant of MCA-38 cells in culture. Lymphocytes were activated with anti-CD3 and cultured with 100 U/ml of IL-2. Various concentrations of supernatant from MCA-38 tumor cultures were titrated into the cell cultures. Cultures were started at 1.5 × 10$^6$ cells/ml and cell counts and cytotoxicity assays were performed on day 3 of culture.

EXAMPLE 8

Expression of RNA Encoding for Cytolytic Proteins Granzyme B and TNF-α

Whole cellular RNA from enriched T lymphocytes from normal mice, and early and late TBM were analyzed at different time points during culture by Northern hybridization in order to assess whether the decreased lytic function of T-AK from late TBM was related to the production of cytolytic effector molecules. Additionally, the CD4+ and CD8+ subsets obtained by depletion were also analyzed. The expression of RNA encoding TNF-α, granzyme B, IL-2, IL-2R, IFN-γ and IL-6 was determined. An 18s RNA was used to determine the relative quantities of RNA loaded onto the gels. To compensate for differences in loading, densitometric ratios between the expression of 18S and granzyme B of TNF-α were done.

The expression levels of IL-2, IL-2R, IFN-γ and IL-6 RNA were identical in the early and late TBM lymphocytes. The level of granzyme B mRNA, however, was 10-fold higher in the CD8+ cells from early TBM at 36 h of culture than in CD8+ from late TBM. The level of granzyme B mRNA in CD8+ cells from late TBM was also significantly lower than in normal CD8+ cells at 36 h as measured by densitometry. The expression of mRNA encoding granzyme B in the CD8+ cells from late TBM increased to levels comparable to that seen in early TBM at 36 h of culture only by day 8 of culture. It is not known whether the cells expressing granzyme B on day 8 in the late TBM cells were a small subset of cells which proliferated to detectable levels by day 8 or whether time in culture allowed the CD8+ cells to recover and regain cytolytic function.

The expression of TNF-α mRNA was also highest in the T lymphocytes of early TBM, measured at 36 h of culture, compared to that of normal mice or late TBM. The expression of TNF-α mRNA in T lymphocytes from late TBM increased to levels comparable to that seen in early TBM at 36 h of culture only by day 8 of culture.

EXAMPLE 9

Marked Changes in the Expression of CD3ζ and CD3γ in T Lymphocytes from Late TBM Expression of the TCR-CD3 complex was also measured by fluorescence intensity of the T cells after labelling with control fluorescein labeled IgG2A, anti-mouse αβ (Pharmingen) or anti-CD3 (145-2Cll). Phenotypic analysis demonstrated that the purified T cells from late TBM were CD3$^+$ (97%), Thy 1.2$^+$ (98%), αβ$^+$ (98%), NK1.1- (<1%) with a normal CD4 (L3T4$^+$)/CDS(Lyt2$^+$) ratio. A comparison of the TCR-CD3 complex of T cells from normal mice and late TBM revealed no apparent changes in the expression of the TCR-CD3 complex as suggested by the fluorescent intensity. The antibodies used for phenotyping the TCR, however, only bind to one each of the seven chains in the TCR-CD3 complex.

Further evaluation of the TCR-CD3 complex was done by surface labeling with $^{125}$Iodine, immunoprecipitation with anti-CD3 (145-2Cll) and resolution by 2-D non-reducing-reducing SDS-PAGE. Approximately 5×10$^7$ T lymphocytes from normal mice and late TBM were labeled with $^{125}$Iodine by the lactoperoxidase-glucose oxidase method. *Current Protocols in Immunology*, Vol. I, J. E. Coligan, A. M. Kruisbeek, D. H. Margulies, E. M. Shevach and W. Strober (eds.), Green Publishing Associates and Wiley-Interscience, 8.11.1-8.11.4 (1991). After labeling, the TCR complexes were precipitated with 145-2Cll MAb, absorbed to protein G-sepharose and resolved by 2D non-reducing-reducing 14% SDS-PAGE. Major changes in the TCR-CD3 components from T cells from late TBM were apparent. The CD3ζ subunit protein was absent and there was a marked decrease in CD3γ. Additionally, a faint spot below the diagonal corresponding to a small protein was present which suggested that an Fcεγ chain was associated with the TCR-CD3 complex. E. Reinherz, *J. Exp. Med.*, 175:203 (1992).

Surface expression of the TCR-CD3 complex of T lymphocytes from normal and late TBM was analyzed. T lymphocytes from normal mice expressed the αβ Ti complex; the δ, ε and γ chains of the CD3; as well and the ζ homodimer. T lymphocytes from late TBM, however, do not express the CD3ζ or CD3γ chains.

Western blots using anti-ζ or anti-Fcεγ confirmed these observations. Approximately 2×10$^7$ T cells from normal and late TBM were solubilized in lysis buffer (25 mM Tris pH7.4, 150 mM NaCl, 0.5% Triton-X 100, 1 mM sodium orthovanadate, 10 μg/ml aprotinin, 10 μg/m; leupeptin and 5 mMEDTA). The lysate was centrifuged and the supernatant was immunoprecipitated with rabbit anti-ζ antiserum, control normal rabbit serum, anti-CD3ε (145-2Cll MAb) or control anti-human CD4 (OKT4). Immunoprecipitate was resolved by SDS-PAGE and blotted with anti-ζ rabbit serum. T lymphocytes from late TBM lost the expression of the ζ chain and expressed the Fcεγ chain normally not seen in T cells. The TCR in T cells from late TBM was therefore αβ, δε, Fcεγ$_2$ instead of the αβ, γδεζ$_2$ seen in normal T lymphocytes. T lymphocytes from early TBM were not tested for TCR-CD3 structure.

Western blot analysis of T lymphocytes from late TBM revealed that ζ protein expression was undetectable in these cells. T lymphocytes from normal mice and early TBM, isolated under the same conditions, expressed normal levels of ζ protein. Thus, an important component in the TCR is absent from the TCR of T lymphocytes from late TBM. The loss of ζ protein expression in T lymphocytes from late TBM is correlated with the loss of in vitro cytotoxic and in vivo immunotherapeutic activity.

T lymphocytes from late TBM, however, expressed normal levels of TCR as determined by immunofluorescence with anti αβ and anti-ε. Western blotting with anti-Fcεγ revealed the unique expression of this member of the ζ family in T lymphocytes from late TBM. The expression of Fcεγ in T lymphocytes from late TBM may explain the presence in these cells of normal levels of TCR in their membrane.

EXAMPLE 10

Aberrant Signal Transduction in Lymphocytes from Late TBM

T lymphocytes from late TBM exhibit an altered form of signal transduction. This is evident from the fact that T lymphocytes from late TBM exhibit a significant decrease in their ability to mobilize Ca$^{2+}$ as compared to T lymphocytes from normal mice or late TBM. Calcium flux was measured in T lymphocytes by calcium sensitive fluorescence and the calcium concentration was estimated according to *Current Protocols in Immunology*, Vol. I, J. E. Coligan, A. M. Kruisbeek, D. H. Margulies, E. M. Shevach and W. Strober (eds.), Green Publishing Associates and Wiley-Interscience, 5.5.1-5.5.15 (1991), incorporated herein by reference. Approximately 1×10$^7$ T cells were loaded with Indo 1 and stimulated with 10 ng/ml anti-CD3 MAb (145-2Cll). Maximal flux was determined after lysis with calcium ionophore. Maximal fluorescence was determined after lysis with Triton-X 100 and minimum fluorescence after calcium chelation with EGTA.

Stimulation of lymphocytes from late TBM with anti-CD3 MAb revealed a significantly decreased ability to mobilize Ca$^{2+}$ as compared to those from normal mice or from early TBM. Even prolonged incubation with anti-CD3 (400 seconds) was not enough to achieve the levels of Ca$^{2+}$ flux seen in T cells from normal or early TBM. Stimulation of T lymphocytes from late TBM with calcium ionophore, however, resulted in equivalent maximum Ca$^{2+}$ flux demonstrating adequate intracellular stores in the cells.

Additionally, the pattern of phosphorylation of tyrosine residues in T lymphocytes from late TBM was markedly different compared to that of cells from normal mice or early TBM. Approximately 1×10$^7$ cells were stimulated in serum free medium with 10 ng/ml of anti-CD3 (145-2Cll) for 2 minutes. The reaction was stopped by washing the cells twice in ice-cold phosphate-buffered saline containing 400 μM sodium orthovanadate and 1 mM EDTA. Cells were lysed in 100 μl of lysis buffer (25 mM Tris pH7.4, 150 mM NaCl, 0.5% Triton-X 100, 1 mM sodium orthovanadate, 10 μg/ml aprotinin, 10 μg/m; leupeptin and 5 mM EDTA) for 5 min. on ice. Lysate were centrifuged and supernatants were analyzed by 10.5% SDS-PAGE under reduced conditions. Proteins were electrophoretically transferred onto PVDF filter (Imobilon-P), blocked with gelatin in TBST buffer (20 mM Tris pH 7.4, 135 mM NaCl, 0.1% Tween 20) and incubated with anti-phosphotyrosine MAb (40 ng/ml). After washing, the blots were incubated with anti-mouse Ig MAb conjugated with peroxidase, subjected to ECL kit (Amersham) and exposed to an X-ray film.

The basal pattern of phosphorylated tyrosine residues was markedly altered in T lymphocytes from late TBM as compared to the other two groups. Changes in the residues in the 40–52 Mr range were consistently seen in three experiments. Stimulation with anti-CD3, however, induced the phosphorylation of tyrosine residues, demonstrating an effective signal transduction.

Figure 4A:
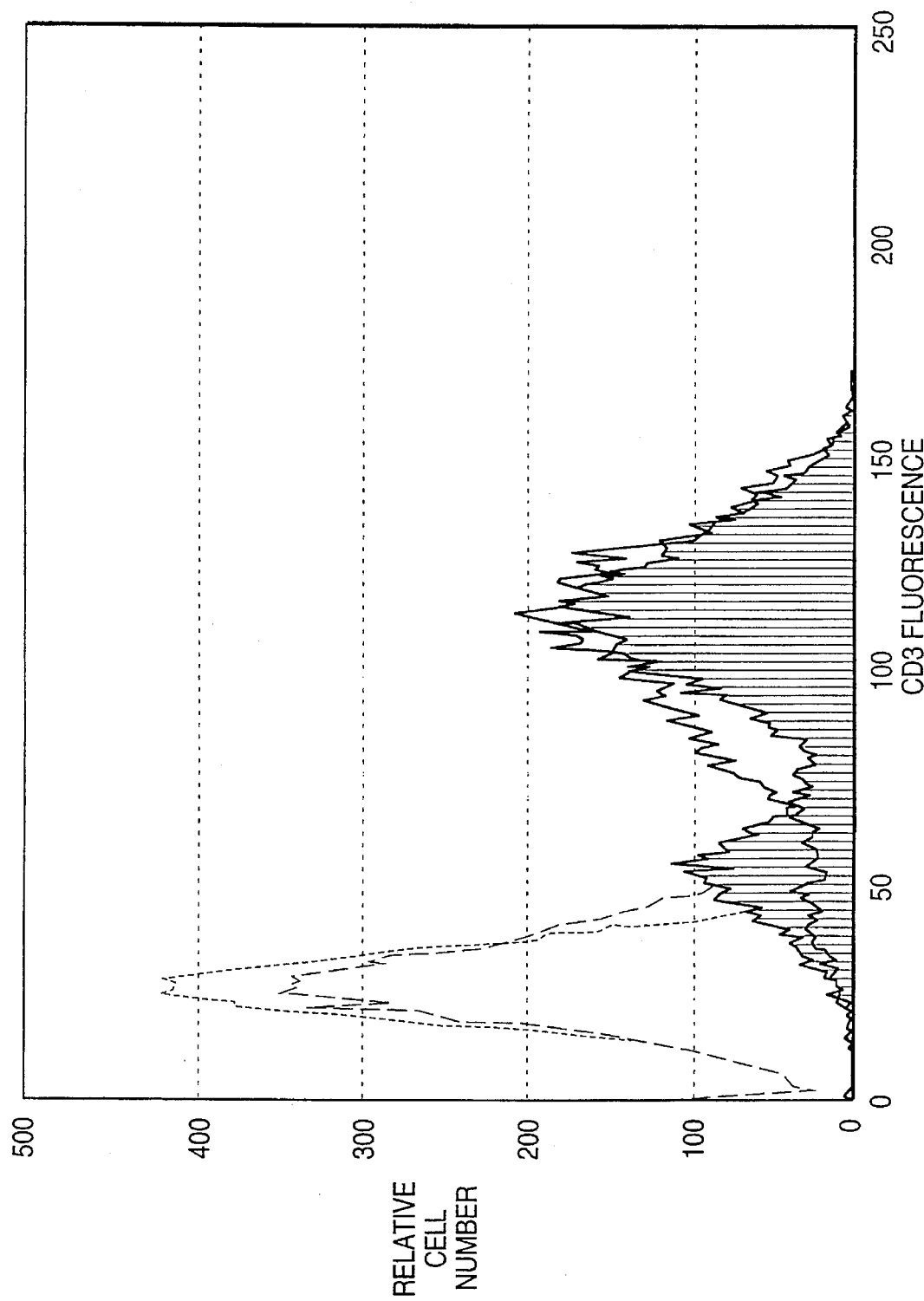
FIG. 4. Surface expression of the TCR-CD3 complex measured by flow cytometry. Isolated T cells from normal and tumor-bearing mice (dotted and dashed lines respectively) were incubated with control fluorescein-labeled $IgG_{2A}$ and (A) antibody to mouse TCRαβ (clone H57-597 Pharmingen) or (B) anti-CD3ε (145-2Cll). Normal mice (shaded); tumor-bearing mice (unshaded).
Figure 4B:
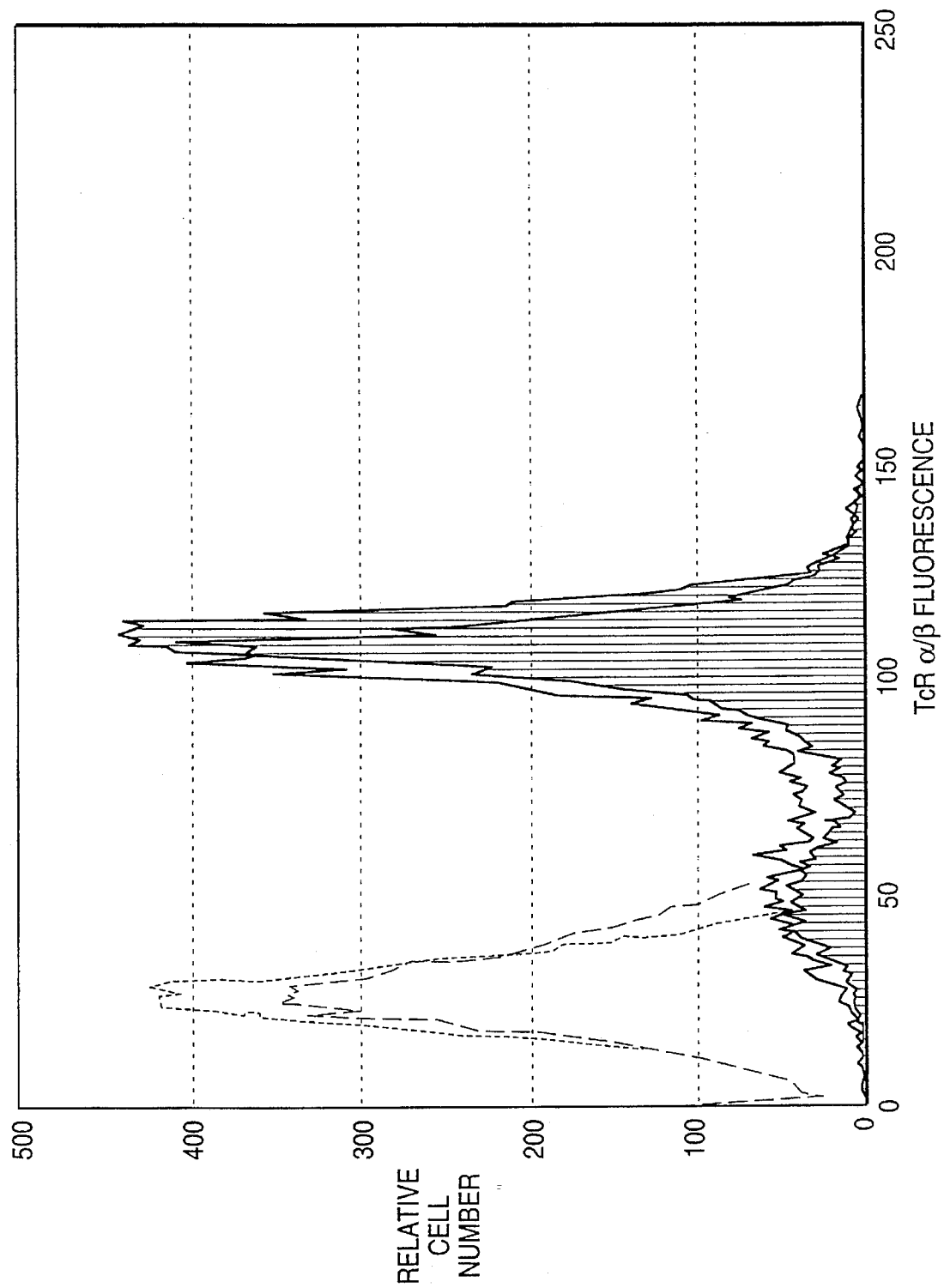

No differences were detected between normal purified splenic T cells and those from tumor-bearing mice in fluorescence intensity (an indicator of receptor number) or in percentage of cells expressing the TCRαB heterodimer (FIG. 4A) or the CD3 complex (FIG. 4B). Flow cytometry demonstrated that splenic T cells from tumor-bearing mice express Thy 1.2 (98%) and TCRαβ 98%), and have a normal CD4/CD8 ratio. They did not express NK cell markers: NK1.1 was <1%. CD16 (Fc receptors) was <1%. No skewing of the T cell receptor repertoire was detected when $V_\beta$ gene usage was examined in splenic T cells. Binding of ligand to the TCR causes $Ca^{2+}$ mobilization. Weiss, (1990), *J. Clin. Invest.* 86, 1015. In contrast to T cells from normal mice, those from tumor-bearing mice had a blunted calcium response when stimulated with monoclonal antibody to CD3 (anti-CD3). The response did not improve with prolonged times of incubation (400 s) (FIG. 4A). However, stimulation with calcium ionophore (Indo-1) resulted in equivalent maximum $Ca^{2+}$ concentration flux in normal T cells and in those from tumor-bearing mice. Thus, the cells from tumor-bearing mice had adequate intracellular $Ca^{2+}$ stores and loading of Indo-1. Analysis of purified $CD4^+$ and $CD8^+$ T cell subsets showed quantitatively similar defects in each subset. These T cells did not optimally release intracellular $Ca^{2+}$ stores in response to signalling through the TCR even though surface TCR density was normal.

EXAMPLE 11

Expression of Lck and Fyn is Undetectable or Diminished in T Lymphocytes from Late TBM Protein tyrosine phosphorylation is the earliest demonstrable event in TCR-mediated signalling, preceding phosphatidylinositol hydrolysis, $Ca^{2+}$ mobilization, and later functional events such as cytokine secretion and cytokine receptor expression (June et al., 1990 *P.N.A.S.* 87:7722, *J. Immunol.* 144:1591; Mustelin et al., *Science* 1990, 247:1584). Because TCR dependent $Ca^{2+}$ flux was impaired, TCR-dependent protein tyrosine phosphorylation was also investigated and found to be altered. The basal pattern of protein tyrosine phosphorylation was altered in T cells from tumor-bearing mice as compared to normal cells.

TCR-mediated signalling was determined in T lymphocytes from tumor-bearing mice. (A) TCR-dependent $Ca^{2+}$ mobilization was determined as follows: T cells ($1\times10^7$) were loaded with Indo-1 and stimulated (t) with anti-CD3 (1 μg/ml). Maximal $Ca^{2+}$ release was determined in cells stimulated with calcium ionomycin. Maximal fluorescence was determined in cells lysed with Triton-X 100 and minimum fluorescence was measured after chelation of $Ca^{2+}$ with EGTA. The concentration of free intracellular $Ca^{2+}$, $[Ca^{2+}]_i$ was measured by methods taught in Grynkiewicz et al. *Biol. Chem.*, 260:3440 (1985). (B) Protein tyrosine phosphorylation was determined as follows: Purified T cells ($10\times10^6$) from normal (N) or tumor-bearing (T) mice were stimulated (+) or left untreated (−) in serum-free medium with 10 μg/ml of purified anti-CD3 for 2 min. The reaction was terminated by washing the cells twice in ice-cold phosphate-buffered saline containing 400 μM sodium orthovanadate and 1 mM EDTA. The T cells were lysed and centrifuged to remove nuclei. Proteins in supernatants were separated by SDS-PAGE, transferred to Immobilon P filters (Millipore), and immunoblotted with antibody to phosphotyrosine, MAb-4G10 (40 ng/ml). (C) Expression of $p56^{lck}$ and $p59^{fyn}$ in T lymphocytes from normal and tumor-bearing mice was determined as follows: Proteins in cell lysates were separated by SDS-PAGE (14% gel), transferred to Immobilon P, and immunoblotted with antiserum to Lck and Fyn peptides (UBI).

Stimulation with anti-CD3 did induce protein tyrosine phosphorylation, but the pattern of proteins phosphorylated was not normal. The abnormal pattern of basal protein tyrosine phos-phorylation in these T cells may have resulted from alterations in the expression of cellular protein tyrosine kinases or in the synthesis of the substrates. Therefore, expression of $p56^{lck}$ and $p59^{fyn}$ two Src family protein tyrosine kinases (PTKs) expressed in T lymphocytes (Varonova and Sefton, 1986, Nature 319:682; Rudd et al. *P.N.A.S.* 1988, 85:5190; Samuelson et al., 1990, *P.N.A.S.* 87:4358), was assessed. Immunoblotting of proteins from whole cell extracts demonstrated a reduction in $p56^{lck}$ and $p59^{fyn}$ in T cells from tumor-bearing mice as compared to normal mice.

Consistent with this altered pattern of phosphorylation in T lymphocytes from late TBM, the expression of Lck in these same cells was markedly decreased. A sample cell lysate, prepared as described above, was run in an 8% SDS-PAGE and blotted with anti-Lck or anti-Fyn rabbit serum. The absence of ζ and the reduction in Lck may alter the signal transduction process, thereby preventing or delaying the activation of the lytic mechanism. Changes in the level of expression in T lymphocytes of ζ, CD3γ and Lck provide markers with which to identify cells capable of activation for adoptive immunotherapy.

In addition to the structural changes in the TCR, the T cells from tumor-bearing mice have a decrease in $p56^{lck}$ and $p59^{fyn}$. Studies with PTK inhibitors have demonstrated the function of such enzymes in TCR-mediated signal transduction (June et al., 1980 loc. cit.). However, proliferation in response to anti-CD3, up-regulation of interleukin-2 receptors, and production of lymphokines (interleukin-2, interleukin-6, interferons) remained normal in T cells from tumor-bearing mice. Thus, lytic function may be more dependent on PTK activity than other lymphocyte functions. Interleukin-2 secretion can be normal in the absence of TCR dependent $Ca^{2+}$ flux.

Supernatants from a variety of tumor cell lines inhibit anti-CD3-induced cytotoxicity by normal T cells in vitro. Precisely the same functional abnormalities and TCR structural abnormalities are observed in T cells from BALB/c mice bearing the RENCA renal cell adenocarcinoma. Thus, these findings are not unique to MCA-38 bearing mice. These findings are likely to be related to the interaction of the tumor and the host in these animals. The molecular changes described herein occur during stages of the disease in both MCA-38- and RENCA-bearing mice when mice are not cachectic or moribund.

EXAMPLE 12

Expression of TCR Subunits

The structure of the TCR was evaluated by surface iodination of purified T cells from normal and tumor-bearing mice. Proteins in the TCR complex were then immunoprecipitated with anti-CD3 and separated by two-dimensional, nonreducing-reducing SDS-polyacrylamide gel electrophoresis (PAGE) (Samuelson et al., 1985 *Cell*, 43:223).

Alterations in the structure of the TCR in T lymphocytes from tumor-bearing mice were determined as follows: Fifty million T lymphocytes were labeled with $Na^{125}I$ by the lactoperoxidase-glucose oxidase method. After labeling, cells were lysed in 1 ml of lysis buffer [25 mMTris (pH 7.4), 300 mM NaCl, 0.5% Triton X-100, 1 mM sodium orthovanadate, 10 μg/ml aprotinin, 10 μg/ml leupeptin and 5 mM EDTA] for 5 min on ice. The TCR complexes were immunoprecipitated from supernatants of cell lysates with anti-CD3 adsorbed to protein G-sepharose and resolved by 2-dimensional non-reducing (NR)-reducing (R) SDS-PAGE (14% gel). The specificity of the subunits immunoprecipitated was confirmed with a cell line (BW5147) that lacks the TCR. Immunoblot analysis of TCRζ and Fcεγ expression were performed as follows: T cells ($20 \times 10^6$) from normal, tumor-bearing mice, BW5147, and 2B4.11 were solubilized and proteins from supernatants of cell lysates were immunoprecipitated with rabbit antiserum to CD3ζ (387) or normal rabbit serum (NRS). Lysates from TCR negative BW5147 thymoma were used. The 2B4.11 hybridoma was used as positive control for Fcεγ. Proteins in immunoprecipitates were blotted with rabbit antiserum to CD3ζ peptide (387) (provided by R. Klausner, NICHD) and antiserum to Fcεγ (provided by J. P. Kinet, NIAID). Blots were developed with peroxidase-conjugated monoclonal antibody to mouse IgG by enhanced chemiluminescence (Amersham).

Both the TCRαβ heterodimer (which migrated below the diagonal because of interchain disulfide bonds) and CD3ε-chain (which migrated above the diagonal because of intrachain disulfide bonds) were present in approximately normal amounts in T lymphocytes from tumor-bearing mice.

In contrast, alterations in other elements of the TCR-CD3 complex were apparent in T cells from tumor-bearing mice. The CD3ζ-chain was absent and the amount of CD3γ-chain was reduced. The failure to detect the ζ-chain in association with the TCR expressed on the cell surface might result from reduced steady state amounts of CD3ζ, aberrant assembly and transport, or instability of detergent solubilized receptor complexes. To determine if detectable levels of CD3ζ protein were present, proteins were immunoblotted from whole cell lysates of splenic T cells. Again, in contrast to normal T cells, the CD3 ζ-chain was absent from T cells of tumor-bearing mice. This result was paradoxical because the TCR is transported to the cell surface inefficiently in the absence CD3 of ζ-chain (Sussman et al., 1989). However, the TCR can be associated with other ζ family members (Orloff et al., 1990). The Fcεγ-chain is a ζ-related protein that subserves ζ-like function in Fc receptor assembly and transport and in signal transduction (Reth, 1989). A protein of smaller molecular size than the ζ-chain was present in the surface labeling experiment that was similar in size to Fcεγ. The presence of this chain in tumor-bearing T cells was confirmed by immunoblotting with antibody to Fcεγ (anti-Fcεγ). Thus, the T lymphocytes from tumor-bearing mice expressed unusual TCR complexes that lacked the CD3ζ-chain, but contained the Fcεγ-chain in the majority of T cells. Abnormal TCR complexes were noted in both CD4+ and CD8+ subsets. The steady state levels of mRNA for lck and CD3ζ chain were normal or elevated suggesting that the defect may be at the post-transcriptional level.

EXAMPLE 13

Assays for Proteins of the TCR subunits and T Lymphocyte Signal Transduction Pathway After Treatment of Tumors with Flavonoids and IL-2

Certain forms of cancer remain invulnerable to attack by therapeutic regimes. For example, renal cell carcinoma (adenocarcinoma) is resistant to conventional chemotherapy. This is a devestating disease because many patients have metastatic disease by the time of diagnosis. Therefore, most of the methods of treatment are ineffective against renal cell carcinoma, although some anti-tumor effects have been observed using biological response modifiers (BRM).

Because some biological response modifiers used individually (α-IFN, IL-2) showed therapeutic efficacy at least as good as conventional chemotherapy, combined modality approaches, including BRM/BRM and BRM/chemotherapy, were pursued to improve efficacy.

Rodent models are useful in identifying therapeutically effective combinations of treatment modalities. Complex experiments involving various permutations in potential therapeutic agents, dose, and administration schedule, may be performed quickly, relatively inexpensively, and without risk to patients. An example of a rodent model is the RENCA system, wherein a RENCA renal adenocarcinoma of Balb/c origin is implanted in an orthotopic site, from which it metastasizes, Murphy and Hrushesky, *J. Natl. Cancer Inst.*, 50:1013 (1980).

Most cytokines are ineffective when used as single agents. The most effective experimental treatments for this tumor include IL-2 in the protocol. Specifically, the use of IL-2 in combination with IFN or cytokine-inducing flavonoids has proved most effective.

In animals that showed tumor reduction, T cells were found to be essential for the anti-tumor response. Moreover, changes in signal transduction molecules associated with tumors, were reversed by therapy. The altered T-cell tyrosine phosphorylated pattern returned to normal, as shown by Western blots. Re-expression of lck and zeta occurred as early as 7 weeks after tumor injection (3–4 weeks after treatment.) TCR and the CD3 complex were not altered.

EXAMPLE 14

Evaluation of Patients for Adaptive Immunotherapy

A patient having renal carcinoma is selected and a lymphocyte preparation is made from peripheral blood to be analyzed for the expression of CD3ζ protein. Lymphocytes are obtained from a healthy individual and prepared and analyzed in the same manner. Peripheral blood lymphocytes are isolated by venipuncture or lymphopheresis. The cells are separated on a Ficoll-Hypaque gradient to obtain mononuclear cells. The cell density of the mononuclear cells thus obtained is determined and equal numbers of cells from the patient and the healthy individual are extracted for protein.

Equal numbers of cells are solubilized in lysis buffer (25 mMTris pH7.4, 150 mM NaCl, 0.5% Triton-X 100, 1 mM sodium orthovanadate, 10 μg/ml aproptinin, 10 μg/m; leupeptin and 5 mMEDTA). The lysate is centrifuged and the supernatant is immunoprecipitated with rabbit anti-ζ antiserum. A control lysate is immunoprecipitated with normal rabbit serum. Immunoprecipitate is resolved by SDS-PAGE, transferred to Nylon membrane (Imobilon-P), and blotted with anti-ζ rabbit serum. A marked reduction in the expression ζ protein in the patient, as compared to the control, is diagnostic of immunosuppression and loss of the ability to use the patient's T lymphocytes in autologous adoptive immunotherapy.

EXAMPLE 14

Protein Expression Changes in Patients with Cancer

In seven of twelve human cancer patients, peripheral blood T cells were found to lack expression of the CD3ζ chain. Some had a decreased expression of Lck and PLCγ. Thus, structural and functional alterations are also noted in T cell signal transduction molecules from tumor-bearing humans.

EXAMPLE 16

Vaccines

In another embodiment, the immunosuppressive factor of the present invention is used in a pharmaceutically acceptable composition that, when administered in an effective amount, is capable of including protective immunity against immunosuppression.

The preparation of vaccines which contain proteins as active ingredients is well understood in the art. Typically, such vaccines are prepared as injectables, either as liquid solutions or suspensions; solid forms suitable for solution in, or suspension in, liquid prior to inject may also be prepared. The preparation may also be emulsified. The active immunogenic ingredient is often mixed with excipient which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents or adjuvants or immunopotentiators which enhance the effectiveness of the vaccine.

The vaccines conventionally are administered parenterally or by injection, for example, either subcutaneously or intramuscularly. Additional formulations which are suitable for other modes of administration include suppositories and, in some cases, oral formulations. For suppositories, traditional binders and carriers may include, for example, polyalkalene glucose or triglycerides; such suppositories may be formed for mixtures containing the active ingredient in the range of 0.5% to 10%, preferably 1.2%. Oral formulations include such normally employed excipients as, for example, pharmaceutical grades of saccharine, cellulose, magnesium carbonate and the like. The compositions take the form of solutions, suspension, tablets, pills, capsules, excipient which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents or adjuvants or immunopotentiators which enhance the effectiveness of the vaccine.

The proteinaceous particles can be formulated into the vaccine as neutral or salt forms. Pharmaceutically acceptable salts, include the acid addition salts (formed with the free amino groups of the peptide) and which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The term "unit dose" refers to physically discrete units suitable as unitary dosages for humans, each unit containing a predetermined-quantity of active material calculated to produce the desired therapeutic effect in association with the required diluent; i.e., carrier, or vehicle.

The vaccines are administered in a manner compatible with the dosage formulation, and in such amount as will be therapeutically effective and immunogenic. The quantity to be administered depends on the subject to be treated, capacity of the subject's immune system to synthesize antibodies, and degree of protection desired. Precise amounts of active ingredients required to be administered depend on the judgement of the practitioner and are peculiar to each individual. However, suitable dosage ranges are of the order of one to several hundred micrograms active ingredient per individual. Suitable regimens for initial administration and booster shots are also variable, but are typified by an initial administration followed in one or two week intervals by a subsequent injection or other administration.

EXAMPLE 17

Diagnostic Systems (Kits)

A diagnostic system, preferably in kit form, useful for detecting the presence of a protein of the present invention protein or antibodies to the protein in a body sample, includes in separate packages, (a) a protein of the present invention which displays antigenicity, and (b) a labeled specific binding agent for signaling the presence of the immunoreaction of the protein of the present invention with antibodies.

A "specific binding agent" is a molecular entity capable of selectively binding a ligand such as a protein of the present invention or an antibody that immunoreacts with a protein of the present invention. Exemplary specific binding agents are antibodies or antibody fragments such as Fab' and $F(ab')_2$, complement fragments, protein A and the like.

In this description, the term "label" in its various grammatical forms refers to single atoms and molecules that are either directly or indirectly involved in the production of a detectable signal to indicate the presence of a immunoreactant. Any labeling means can be linked to, or incorporated in, a specific binding agent or used separately, and those atoms or molecules can be used alone or in conjunction with additional reagents. Such labels are themselves well-known in immunochemistry and constitute a part of this invention only insofar as they are utilized with otherwise novel proteins methods and/or systems.

The diagnostic kits of the present invention are typically used in an "ELISA" format to detect the presence of quantity of antibodies in a body sample such as serum or plasma. "ELISA" refers to an enzyme-linked immunosorbent assay that employs an antibody or antigen bound to a solid phase and an enzyme-antigen or enzyme-antibody conjugate to detect and quantify the amount of antigen or antibody present in a sample. A description of the ELISA technique is found in Chapter 22 of BASIC AND CLINICAL IMMUNOLOGY (4th ed. 1982) by D. P. Sites et al., published by Lange Medical Publications of Los Altos, Calif., and in U.S. Pat. Nos. 3,654,090, 3,850,752 and 4,016,043, the respective contents of which are incorporated herein by reference.

Thus, in preferred embodiments the protein displaying antigenicity is affixed to a solid matrix to form a solid support. Typically, the protein can be affixed to the solid matrix by adsorption from an aqueous medium although several modes of adsorption from an aqueous medium as well as other modes of affixation, well known to those skilled in the art can be used. Exemplary of such modes are the reaction of the receptor or antigen with the reactive carboxyl functionality produced by the reaction of cyanogen bromide with glucose-containing matrices such as cross-linked dextrose or cellulose, glutaraldehyde linking as discussed hereinafter in conjunction with latex particles and the like.

Useful solids are well known in the art. Such materials include the cross-linked dextran available under the trademark SEPHADEX from Pharmacia Fine Chemicals (Piscataway, N.J.); agarase; beads of polystyrene beads about 1 micron to about 5 millimeters in diameter available from Abbott Laboratories of North Chicago, Ill.; polyvinyl chloride, polystyrene, cross-linked polyacrylamide, nitrocellulose of nylon-based webs such as sheets, strips or paddles; or tubes, plates or the wells of a microtiter plate such as those made from polystyrene or polyvinylchloride.

In a preferred embodiments, the kit further includes, in a separate package, an amplifying reagent such as complement, like guinea pig complement, anti-immunoglobulin antibodies or *S. aureus* cowan strain protein A that reacts with the antigen or antibodies being detected. In these embodiments, the label specific binding agent is capable of specifically binding the amplifying means when the amplifying means is bound to the protein or antibody.

The label specific binding agent of any diagnostic system described herein, as well as the above-described amplifying reagent, may be provided in solution, as a liquid dispersion or as a substantially dry powder, for example, in lyophilized form. Where the indicating means is an enzyme, the enzyme's substrate can also be provided in a separate package of the system. A solid support such as a microtiter plate and one or more buffers can also be included as separately packaged elements in this diagnostic assay system.

The packages discussed herein in relation to diagnostic systems are those customarily utilized in diagnostic system. Such packages include glass and plastic (e.g., polyethylene, polypropylene and polycarbonate) bottles, vials, plastic and plastic-foil laminated envelopes and the like.

EXAMPLE 18

The Pattern of NF-κB/rel Transcription Factors is Altered in an Animal Tumor Model, and Reversed by Therapy An impaired immune system has been documented both in a cancer patient and in tumor-bearing mice. Among the contributing factors for the immune impairment, T-cell function plays an important role. In order to investigate the T-cell condition in a tumor bearing mammal, a spontaneously arising renal cell carcinoma (Renca) model from a BALB/c mouse was used. This tumor model has two important features: (1) the metastatic pattern displayed by Renca is similar to human renal cell carcinoma, Golumbek et al. (1991) "Treatment of Established Renal Cancer by Tumor Cells and Engineered to Secrete Interleukin-4" and (2) it has been shown in this murine model that the experimental drug Flavone-8-acetic acid (FAA) in combination with rIL-2 cures 80% of mice bearing established Renca tumors, and that these mice have successfully responded to subsequent rechallenge. Wiltrout et al. (1988) "Flavone-8-Acetic Acid Augments Systemic Natural Cell Activity and Synergizes with IL-2 for the Treatment of Murine Renal Cancer," (1988) *J. Immunol.* 140(9):3261.

When nuclear extracts of normal splenic T-cells were examined in Western blot analysis using anti-c-rel, anti-p65, and anti-p50 antisera, normal levels of all three proteins were observed. In contrast, nuclear extracts of splenic T-cells from tumor-bearing mice were devoid of c-rel and p65. Unexpectedly, in place of p50, two shorter forms of the protein (p48 and p44), where "48" and "44" refer to estimated approximate molecular weights of 48 and 44 kD respectively, as determined by gel electrophoresis, were observed in the nucleus.

The specificity of antisera against c-rel, p65 and p50, was demonstrated by competition with the respective peptides. Although the shorter forms of p50 were present exclusively in the nucleus, normal sized protein was present in the cytoplasm. When the same extracts were analyzed for p50 using an antiserum made against an N-terminal peptide of the protein, no shorter form of p50 was detected, although this antiserum was able to detect normal p50. The interpretation of these results is that the shorter forms of p50 are due to the N-terminal truncation of the protein. These new forms of p50 could also result from alternate splicing, although no shorter form of the precursor molecule, p105, was observed in the cytoplasmic fraction of the tumor sample.

In order to determine whether absence of nuclear c-rel and p65, and presence of alternate forms of p50 in splenic T-cells from tumor-bearing mice correlated with the presence of a tumor, splenic T-cells from FAA/IL-2treated animals sampled at various time points after treatment, were analyzed by Western blot. Treatment of tumor-bearing mice with FAA was initiated at 7 days. IL-2 was administered on each of days 8–10 days. Eleven days later, splenic T-cells showed the same pattern as an untreated tumor-bearing group of mice with respect to nuclear c-rel, p65 and p50. In contrast, splenic T-cells from animals treated with FAA and IL-2 for another week showed approximately normal levels of nuclear c-rel, p65 and p50. Interestingly, shorter forms of p50 were no longer present in the treated group. No sign of visible tumor was observed either by macroscopic or microscopic analysis in treated animals four weeks after tumor initiation, that is, three weeks after treatment. The untreated tumor-bearing group normally dies at about day 35. Analysis of splenic T-cells from mice exhibiting long term survival, defined as surviving to week 7, showed that the nuclear levels of rel family members were normal.

When the nuclear extracts of splenic T-cells from normal and tumor-bearing animals were used in an electrophoretic mobility shift assay (EMSA) Tan, T. H. et al., "Purification and characterization of multiple nuclear factors that bind to the TAX-inducible enhancer within the human T-cell leukemia virus type 1 long terminal repeat." (1989) *Mol. Cell. Biol.* using an oligonucleotide from an immunoglobulin heavy chain gene, the patterns of DNA-protein complexes differed in tumor samples compared to non-tumor bearing samples. As compared to the normal pattern, two faster migrating complexes were observed. Both of these complexes were specific to the nucleotide probe as revealed by competition analysis with specific and non-specific oligonucleotides. These new DNA-protein complexes also correlated with the status of the tumor, as revealed by the reappearance of the normal pattern in samples from the group assessed four weeks after tumor initiation.

In order to characterize the nature of the DNA-protein complexes in tumor samples, UV-crosslinking Kochel et al., "V-rel and C-rel-Protein Complexes Bind to the NF-κB site In Vitro," *Oncogene* (1992) 7:567–572 and immunoprecipitation, Rice et al. (1992) *Cell,* 71:243–263, of the crosslinked product were performed. In a normal sample, the slower migrating DNA-protein complex consisted of two proteins corresponding to a combination of a p50 and p65, whereas the faster migrating complex consisted of a protein corresponding to p50, as has been shown before Sang-Mo Kang et al., "NF-κB Subunit Regulation in Nontransformed CD4+T Lymphocytes" (1992) Science 256:1452. In a tumor sample, the upper DNA-protein complex consisted of a protein which was shorter than p50, and the lower complex consisted of two proteins corresponding to two shorter derivatives of p50. UV-crosslinked products were immunoprecipitated with different anti-p50 antisera. When immunoprecipitation was done with normal samples, the slower migrating complex was found to be precipitated with two different anti-p50 and one anti-p65 antiserum. These results indicated that the upper complex consisted of p50 an p65. The faster migrating complex was found to be precipitated by three different anti-p50 antisera, which indicated that the lower complex consisted of p50.

When tumor samples were analyzed, the slower migrating complex was found to be precipitated by two different anti-p50 antisera, but not by the third antiserum which was made against the N-terminal peptide. Based on the molecular weight of the precipitated molecule, it was concluded that the upper complex consisted of p48. Similarly, the faster migrating complex was found to be precipitated by the same two anti-p50 antisera as in the upper complex, but not by the antiserum made against the N-terminal peptide. In this case, two proteins were obtained that correspond to p48 and p44, corresponding to the anti-peptide antisera. No protein band was obtained when immunoprecipitation was done with preimmune sera.

MATERIALS AND METHODS

Stimulation of T Lymphocytes

In an illustrative embodiment, T lymphocytes are stimulated with an antibody to a lymphocyte surface receptor in vitro, for short time periods. Optionally, one or more cytokines also are present during stimulation. The time periods for stimulation are less than about 24 hours, for as little as 30 minutes, and generally for 12–18 hours. These stimulated cells have a high therapeutic efficacy when injected in vivo. Stimulation by anti-CD3 induces the expression of the IL-2 receptor. Anti-CD3-stimulated cells are less toxic than cells cultured in IL-2 for several days because the anti-CD3-stimulated cells cause less acute pulmonary toxicity. Similarly, because anti-CD3 stimulated cells can multiply in number in the presence of IL-2, small numbers of injected anti-CD3 stimulated cells can proliferate to large numbers following in vivo exposure to IL-2. Thereby, fewer cells need to be administered when IL-2 is present, to achieve sufficient numbers of anti-CD3 stimulated cells.

Alternatively, T lymphocytes are stimulated in vitro with antibodies directed to more than one lymphocyte surface receptor. Optionally, one or more cytokines are be also be present during stimulation. The stimulation of T lymphocytes in vivo can also be accomplished with antibodies to one or more T lymphocyte surface receptors; with one or more cytokines; or with a combination of antibodies and cytokines.

Kinase Reaction Assay

Lyse 107 cells in a standard manner

Immunoprecipitate with anti-Fyn Ab (6, μl), anti-Lck Ab (3 μl)

Wash 3× with washing buffer without EDTA

Wash 1× kinase buffer without ATP

Add 30 μl of kinase buffer plus 10–20 μCi of [γ-$^{32}$P]ATP (3300 Ci/mmol) (3–5 μl) and 1 μM ATP Incubate R/T for 10 min.

Wash 3× with washing buffer containing 20 mM EDTA

Elute 1.5× sample buffer

Run 8% of gel

Fix the gel in 10% AcAcid and 50% MtOH for 30 min.

Replace with 3% glycerol for 20 min.

Dry up the gel using the gel dryer for 1.5 hr.

Expose the gel to X-ray film

* Kinase Buffer

-continued 100 mM NaCl
20 mM HEPES, pH 7.5
5 mM MnCl$_2$
5 mM MgCl$_2$

1 μM ATP
3–5 μl of [γ-$^{32}$p]ATP

Methods for Producing Antibodies

An antibody to a T lymphocyte surface receptor protein or to the soluble immunosuppressive factor can be made by well known and conventional methods, for example those described in *Current Protocols in Immunology*, Vol. I, J. E. Coligan, A. M. Kruisbeek, D. H. Margulies, E. M. Shevach and W. Strober (eds.), Green Publishing Associates and Wiley-Interscience, 2.4.1-2.10.3 (1991), which is incorporated herein by reference.

A monoclonal antibody is prepared which is directed toward the factor. The antibody is developed using supernatants from tumor preparations as an immunogen, and techniques known to those of skill in the art. The monoclonal antibody is useful in purifying the factor by affinity chromatography (Marlow and Lane Antibodies Manual).

Antibodies to a surface receptor are used alone, or in combination with other antibodies to different T cell surface receptors to activate T lymphocytes. Suitable antibodies include anti-CD2, anti-CD3, anti-CD4, anti-CD5, anti-CD6, anti-CD7, anti-CD8, anti-CD28, anti-CDw29, and anti-CD45R. A preferred antibody is anti-CD3 monoclonal antibody (MAb). An anti-CD3 MAb includes OKT3, WT32, Leu-4, SPV-T3c, RIV9, 64.1, 145-2Cll, and the like. More preferably, the anti-CD3 MAb is the anti-murine CD3 MAb 145-2Cll, which has been identified by Leo et al, *Proc. Natl. Acad. Sci. USA*, 84, 1374 (1978), and is available from the American Type Culture Collection (ATCC). Mouse anti-human OKT3 is available from the Ortho Division of Johnson and Johnson. Versions of the antibodies derived from humans are useful for T cell activation in vivo during treatment. T lymphocytes treated with anti-CD3 MAb for less than about 24 hours are preferably treated with a total dose of about 10/ng/ml, or less.

Isolation and Purification of the Soluble Immunosuppressive Factor

The immunosuppressive factor is purified from supernatants of tumor cell preparations by sequential gel filtration, anion and cation exchange, and FPLC. These methods are known to those of skill in the art. The final purification steps may require HPLC using ion exchange or reverse phase chromatography. Polypeptide fragments of the isolated factor are tested to determine which fragments retain the immunosuppressive activity. The amino acid sequences of those polypeptide fragments are determined. Degenerate oligonucleotides are then derived from the amino acid sequences and used to clone the factor using techniques described by Maniatis (1982). (Molecular Cloning, a Laboratory Manual, Cold Spring Harbor, N.Y.).

What is claimed is:

1. A method of determining the level of immunosuppression in a mammal, said method comprising the steps of:

a) determining the pattern of transcription factors of the NF-κB/rel family in a nuclear extract of a T lymphocyte preparation from a mammal; and b) comparing said pattern with the pattern characteristic of a comparable T lymphocyte preparation from a non-immunosuppressed individual of the same mammalian species, a significant departure from the pattern in the non-immunosuppressed individual indicating a significant degree of immunosuppression in the mammal.

2. The method of claim 1, wherein the pattern is determined by presence or absence of c-rel/p65, p50, p48 and p44.

3. The method of claim 1, wherein said T lymphocyte preparation is prepared from tissue comprising spleen tissue, peripheral blood, tumor tissue, lymph node tissue, cerebrospinal fluid, pleural effusions and ascites.

4. A method of identifying a patient having T lymphocytes capable of activation for immunotherapy, said method comprising the steps of:

a) determining the pattern of transcription factors of the NF-κB/rel family in a nuclear extract of T lymphocytes from the patient;

b) comparing said pattern with the pattern characteristic of a non-immunosuppressed individual; and c) selecting a patient whose pattern is above a therapeutically effective threshold in a non-immunosuppressed individual.

5. The method of claim 4, wherein said T lymphocytes are derived from tissue comprising spleen tissue, peripheral blood, tumor tissue, lymph node tissue, cerebrospinal fluid, pleural effusions and ascites.

6. In a method of treating a patient who has a disease responsive to immunotherapy, wherein said patient is treated with stimulated T lymphocytes, the improvement wherein said patient is identified by the method according to claim 4.

7. The method of claim 6, wherein said disease is cancer.

8. The method of claim 6 wherein said cancer is melanoma.

9. A method of identifying an agent which causes immunosuppression of mammalian T lymphocytes, said method comprising the steps of:

a) providing a mammalian T lymphocyte preparation wherein the pattern of transcription factors of the NF-κB family in a nuclear extract of the sample is characteristic of a non-immunosuppressed individual of a mammalian species;

b) culturing said lymphocyte preparation in the presence of a suspected immunosuppressive agent;

c) determining the pattern of transcription factors of the NF-κB family in a nuclear extract of the cultured preparation; and d) identifying an agent which causes a significant alteration in the pattern from the pattern of the preparation not cultured in the presence of the agent.

10. A method of identifying an agent which reverses immunosuppression of mammalian T lymphocytes, said method comprising the steps of:

a) providing a mammalian T lymphocyte preparation from an immunosuppressed mammal, wherein the pattern of the transcription factors of the NF-κB family in a nuclear extract of the preparation is significantly altered from the pattern characteristic of a comparable sample from a non-immunosuppressed individual of the same mammalian species;

b) culturing said lymphocyte preparation in the presence of an agent suspected of reversing immunosuppression;

c) determining the pattern of the transcription factors of the NF-κB family in a nuclear extract of the culture;

d) identifying an agent which causes a significant alteration in the pattern wherein the altered pattern does not show a significant departure from the pattern characteristic of a comparable sample from a non-immunosuppressed individual of said mammalian species.

11. The method of claim 10, wherein the agent is present in vivo.

* * * * *